(12) United States Patent
Yu et al.

(10) Patent No.: US 8,058,258 B2
(45) Date of Patent: Nov. 15, 2011

(54) METHODS FOR CANCER THERAPY AND STEM CELL MODULATION

(75) Inventors: Qiang Yu, Singapore (SG); Jing Tan, Singapore (SG); Xiao Jing Yang, Singapore (SG)

(73) Assignee: Agency for Science, Technology and Research, Centros (SG)

( * ) Notice: Subject to any disclaimer, the term of this patent is extended or adjusted under 35 U.S.C. 154(b) by 407 days.

(21) Appl. No.: 12/281,470

(22) PCT Filed: Nov. 15, 2006

(86) PCT No.: PCT/SG2006/000350
§ 371 (c)(1),
(2), (4) Date: Sep. 2, 2008

(87) PCT Pub. No.: WO2007/100304
PCT Pub. Date: Sep. 7, 2007

(65) Prior Publication Data
US 2010/0075915 A1    Mar. 25, 2010

Related U.S. Application Data

(60) Provisional application No. 60/778,532, filed on Mar. 2, 2006.

(51) Int. Cl.
*A01N 43/04* (2006.01)
*A61K 31/70* (2006.01)

(52) U.S. Cl. ............................................. 514/45; 514/43

(58) Field of Classification Search ........................ None
See application file for complete search history.

(56) References Cited

U.S. PATENT DOCUMENTS

| | | | |
|---|---|---|---|
| 510,260 A | 12/1893 | Higham | |
| 4,968,690 A | 11/1990 | Marquez et al. | |
| 5,843,780 A | 12/1998 | Thomson | |
| 6,090,622 A | 7/2000 | Gearhart et al. | |
| 2005/0176142 A1 | 8/2005 | Nakorn et al. | |
| 2005/0244417 A1 | 11/2005 | Ashkenazi et al. | |
| 2005/0245559 A1 | 11/2005 | Koul et al. | |
| 2005/0266093 A1 | 12/2005 | Mohapatra | |
| 2006/0147456 A1 | 7/2006 | Lebecque et al. | |

FOREIGN PATENT DOCUMENTS

| | | |
|---|---|---|
| WO | WO-90/09177 | 8/1990 |
| WO | WO-2004046312 A2 | 6/2004 |

OTHER PUBLICATIONS

Oxenrider et al. FEBS Letters (1993), vol. 316, pp. 273-277.*
Moon et al. Bioorganic & Medicinal Chemistry Letters (2004), vol. 14, pp. 5641-5644.*
Beisel, et al, Histone methylation by the *Drosophila* epigenetic transcriptional regulator Ash1, Nature, Oct. 2002, vol. 419, pp. 857-862.
Boyer, et al., "Polycomb complexes repress developmental regulators in murine embryonic stem cells," Nature, vol. 441, May 18, 2006, doi:10.1038, pp. 349-353.
Bracken, et al, EXH2 is downstream of the pRB-E2F pathway, essential for proliferation and amplified in cancer, The EMBO Journal, 2003, vol. 22 No. 20, pp. 5323-5335.
Bracken, Genes Dev. 2006,20 1123-1136.
Bray, et al., "3-Deazaneplanocin A induces massively increased interferon-γ production in Ebola virus-infected mice," Antiviral Research, 55 (2002), pp. 151-159.
Brown, R, Trends in Molecular Medicine (2002), 8,4,S43-S48.
Cao, et al, SUZ12 Is Required for Both the Histone Methyltransferase Activity and the Silencing Function of the EED-EZH2 Complex, Molecular Cell, Jul. 2, 2004, vol. 15, pp. 57-67.
Cao, et al., Role of Histone H3 Lysine 27 Methylation in Polycomb-Group Silencing, Science, 2002, 298, pp. 1039-1043.
Chambers, I. Smith, Oncogene 2004, 23, 7150-7160.
Chen, et al, Down-regulation of Human DAB2IP Gene Expression Mediated by Polycomb Ezh2 Complex and Histone Deacetylase in Prostate Cancer, The Journal of Biological Chemistry, vol. 280 No. 23, Jun. 10, 2005, pp. 22437-22444, USA.
Chiang, Journal of Biological Chemistry, vol. 267, No. 7 (1992) pp. 4988-4991.
Collins, et al., "Stem Cell Function, Self-Renewal and Behavioral Heterogeneity of Cells from the Adult Muscle Saellite Cell Niche," Cell, vol. 122, Jul. 29, 2005, pp. 289-301.

(Continued)

*Primary Examiner* — Patrick Lewis
(74) *Attorney, Agent, or Firm* — Choate, Hall & Stewart, LLP

(57) ABSTRACT

The present invention relates to a method of inducing apoptosis in a tumour cell as well as modulating pluripotency and/or self-renewing characteristics of a stem/progenitor cell. The method comprises administering to the respective cell a compound of general formula (I). In general formula A is C or N. $R^1$, $R^4$ and $R^5$ are, independently selected, H or aliphatic, cycloaliphatic aromatic, arylaliphatic, or arylcycloaliphatic hydrocarbyl groups, that comprise 0-3 heteroatoms being N, O, S, or Si. $R^4$ and $R^5$ may optionally be linked so as to define an aliphatic hydrocarbyl bridge. $R^2$ is H or a halogen, such as F or Cl. $R^3$ is H, or an aliphatic or arylaliphatic hydrocarbyl group comprising 1-8 main chain carbon atoms and 0-3 heteroatoms being N, O, S, Si, or a halogen such as Cl or F. Also provided is a pharmaceutical composition for inducing apoptosis in a tumour cell and/or modulating pluripotency and/or self-renewing characteristics of a stem/progenitor cell. The pharmaceutical composition comprises a compound as defined above or a pharmaceutically acceptable salt thereof and a carrier or diluent.

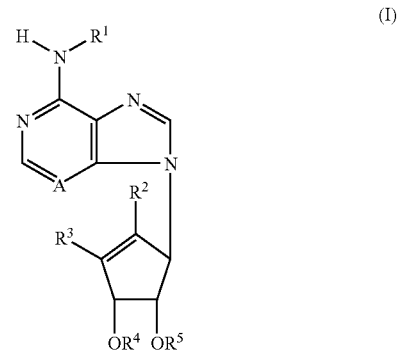

(I)

26 Claims, 17 Drawing Sheets

OTHER PUBLICATIONS

Costa, Non-coding RNAs: New players in eukaryotic biology, Gene, 2005, vol. 357, pp. 83-94.
De Clercq, Erik, "Vaccinia Virus Inhibitors as a Paradignm for Chemotherapy of Poxvirus Infections," Clinical Microbiology Review, Apr. 2001, pp. 382-397.
De Clercq, et al., "Broad-Spectrum Antiviral and Cytocidal Activity of Cyclopentenylcytosine, A Carbocyclic Nucleoside Targeted at CTP Synthetase," Biochemical Pharmacology, 1999, vol. 41, No. 12 pp. 1821-1829.
De Clercq, Biochemical Pharmacology, vol. 41, No. 12 (1991) p. 1821-1829.
Driscoll, Stem Cells vol. 12 No. 1 (1994) pp. 7-12.
Feinberg, A.P., Nature Review Genetics (2006) pp. 7, 21-33.
Glazer, et al., "3-Deazaneplanocin: A new and potent inhibitor of S-Adenosylhomocysteine Hydrolase and its effects on human promyelocytice leukemia cell line HL-60," Biochemical and Biophysical Research Communications, Mar. 13, 1986, vol. 135 No. 2, pp. 688-694.
Hayashi, M. Nucleic Acids Symposium Series No. 8 (1980 65-67.
Holden, Gene-Srppressing Proteins Reveal Secrets of Stem Cells, Science, Apr. 21, 2006, vol. 312, p. 349.
Kalantry, et al, The Polycomb group protein Eed protects the inactive X-chromosome from differentiation-induced reactivation, Nature Cell Biology, Feb. 2006, vol. 8 No. 2, pp. 195-202.
Kamminga, et al, The Polycomb group gene Ezh2 prevents hematopoietic stem cell exhaustion, Blood Journal, Mar. 1, 2006, vol. 107 No. 5, pp. 2170-2179.
Kim, et al, Korean Journal of Biochemistry vol. 20 No. 2 (1988) p. 85-92.
Kirmizis, et al, Identification of the Polycomb Group Protein SU(Z)12 as a Potential Molecular Target for Human Cancer Therapy, Molecular Cancer Therapeutics, Jan. 2003, vol. 2, pp. 113-121.
Kirmizis, et al, Silencing of human polycomb target genes is associated with methylation of histone H3 Lys 27, Genes & Development, 2004, vol. 18, pp. 1592-1605.
Krivtsov, et al., "Transformation from committed progenitor to leukemia stem cell initiated by MLL-AF9" Nature, Aug. 2006, vol. 442, pp. 818-822.
Kuzmichev, Andrei, "Composition and histone substrates of polycomb repressive group complexes change during cellular differentiation," PNAS, Feb. 8, 2005, vol. 102, No. 6, 1859-1864.
Kusmichev, "Different Ezh2-containing complexes target methylation of histone H1 or nucleosomal Histone H3", Molecular Cell, 2004, 14, 2, 382-397.
Lee, et al, Control of Developmental Regulators by Polycomb in Human Embryonic Stem Cells, Cell, Apr. 21, 2006, pp. 301-313.
Levine, et al., Division of labor in Polycomb group repression, TRENDS in Biochemical Sciences, Sep. 2004, vol. 29, pp. 478-485.
Lund, et al., Polycomb complexes and silencing mechanisms, Science Direct, 2004, pp. 239-246
Maitra, Nature Genetics (2005) 37, 18, 1099-1103.
Milne, et al., MLL Targets SET Domain Methyltransferase Activity to *Hox* Gene Promoters, Molecular Cell, Nov. 2002, vol. 10, pp. 1107-1117.
Mitsui, et al, The Homeoprotein Nanog Is Required for Maintenance of Pluripotency in Mouse Epiblast and ES Cells, Cell, May 30, 2003, vol. 113, pp. 631-642.
Moon et al, Bioorganic & Medicinal Chemistry Letters vol. 14, No. 22 (2004) pp. 5641-5644.
Morrissey, et al, Potent and persistent in vivo anti-HBV activity of chemically modified siRNAs, Nature Biotechnology, Aug. 2005, vol. 23 No. 8, pp. 1002-1007.
Muller, et al., Histone Methyltransferase Activity of a *Drosophila* Polycomb Group Repressor Complex, Cell Press, Oct. 2002, vol. 111, pp. 197-208.
Nichols, et al, Formation of Pluripotent Stem Cells in the Mammalian Embryo Depends on the POU Transcription Factor Oct4, Cell, Oct. 30, 1998, vol. 95, pp. 379-391.
Pasini, et al., "Suz12 is essential for mouse development and for EZH2 histone methyltransferase activity," The EMBO Journal (2004) 23, 4061-4071.
Passegue, Proc. Natl. Acad. Sci. USA (2003), 100, 11842-11849.

Patzel, Design of siRNAs producing unstructured guide-RNAs results in improved RNA interference efficiency, Nature Biotechnology, Nov. 2005, vol. 23 No. 11, pp. 1440-1444.
Peedicayil, Epigenetic therapy—a new development in pharmacology, Indian J Med Res, Jan. 2006, vol. 123, pp. 17-24.
Rando, Thomas A., "The adult muscle stem cell comes of age," Nature Medicine, Aug. 2005, pp. 829-831.
Reynolds, et al, Tumor Suppressor p16INK4A Regulates Polycomb-mediated DNA Hypermethylation in Human Mammary Epithelial Cells, The Journal of Biological Chemistry, Aug. 25, 2006, vol. 281 No. 32, pp. 24790-24802, USA.
Santos, F. Reproduction (2004) vol. 127, pp. 643-651.
Saramaki, et al, The Gene for Polycomb Group Protein Enhancer of Zeste Homolog 2 (EZH2) is Amplified in Late-Stage Prostate Cancer, Genes, Chromosomes & Cancer, 2006, vol. 45, pp. 639-645.
Schoeftner, et al, Recruitment of PRC1 function at the initiation of X inactivation independent of PRC2 and silencing, The EMBO Journal, 2006, vol. 25 No. 13, pp. 3110-3122.
Schuldiner, et al., Induced neuronal differentiation of human embryonic stem cells, Brain Research 913, (2001), pp. 201-205.
Song, et al, Antibody mediated in vivo delivery of small interfering RNAs via cell-surface receptors, Nature Biotechnology, Jun. 2005, vol. 23 No. 6, pp. 709-717.
Sparmann, et al., Polycomb silencers control cell fate, development and cancer, Nature Reviews Cancer, Nov. 2006, vol. 6, pp. 846-856.
Squazzo, et al, Suz12 binds to silenced regions of the genome in a cell-type-specific manner, Genome Research, 2006, vol. 16, pp. 890-900.
Thomson, J. A., Embryonic Stem Cell Lines Derived from Human Blastocysts, Science 282, 1145 (1998), 282, 1145-1147.
Tseng, et al., "Synthesis of 3-Deazaneplanocin A, a Powerful Inhibitor of S-Adenosylhomocystein Hydrolase with Potent and Selective in Vitro and in Vivo Antiviral Activities," Journal of Medicinal Chemistry, 1989, vol. 32 No. 7, pp. 1442-1446.
Tsujino, Curr. Chemother. Infect. Dis., Proc. Int. Congr. Chemother. vol. 2 (1980) pp. 1559-1561.
Vire, Nature (2006) 439, 16 871-874.
Vizirianakis, I.S. Review of Clinical Pharmacology and Pharmacokinetics International Edition vol. 18 No. 1 (2004) pp. 40-42.
Weissleder, et al, Cell-specific targeting of nanoparticles by multivalent attachment of small molecules, Nature Biotechnology, Nov. 2005, vol. 23 No. 11, pp. 1418-1423.
Xiang, et al, Short hairpin RNA-expressing bacteria elicit RNA interference in mammals, Nature Biotechnology, Jun. 2006, vol. 24 Bumbre 6, pp. 697-702.
Yoo, C.B., Nature Reviews Drug Discovery (2006) 5,1,37-50.
Yu, et al, The porcine FBXO32 gene: map assignment, SNP detection and tissue expression, Animal Genetics, 2005, vol. 36 No. 5, pp. 435-462.
Zamore, Ribo-gnome: The Big World of Small RNAs, Science, 2005, vol. 309, pp. 1519-1524, Washington, DC, USA.
Cameron, et al., "Synergy of demethylation and histone deacetylase inhibition in the re-expression of genes silenced in cancer," Nature Genetics, 21: 103-107, 1999.
Gore, Steven D., "Combination therapy with DNA methyltransferase inhibitors in hematologic malignancies," Nature Clinical Practice; 2(Supp 1): S30-S35, 2005.
Supplemental European Search Report for EP06813130, mailed on Jun. 24, 2010.
Tan, et al., "Phamacologic disruption of Polycomb-repressive complex 2-mediated gene repression selectively induces apoptosis in cancer cells," Genes & Development, 21(9): 1050-1063, 2007.
Verschuur, et al., "Cyclopentenyl cytosine induces apoptosis and increases cytarabine-induced apoptosis in a T-lymphoblastic leukemic cell-line," Leukemia Research 25(10): 891-900, 2001.
Whaun, et al., "Effects of 3-Deazaneplanocin A on DS-19 Friend Erythro-Leukemia Cells," Faseb Journal, 8(4-5); A904, 1994.

* cited by examiner

| MG132 | − | − | + | − | − |
| LLNL | − | − | − | + | − |
| MG115 | − | − | − | − | + |
| DZNep | − | + | + | + | + |

EZH2

SUZ12

Actin

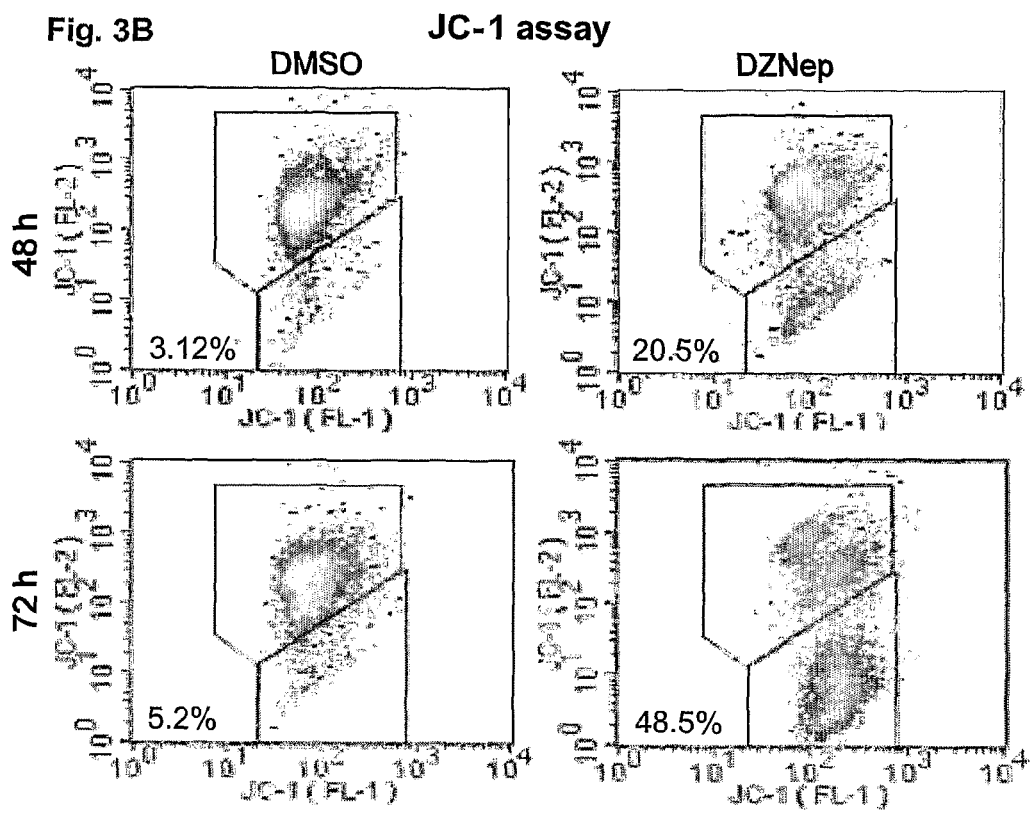
Fig. 3B  JC-1 assay
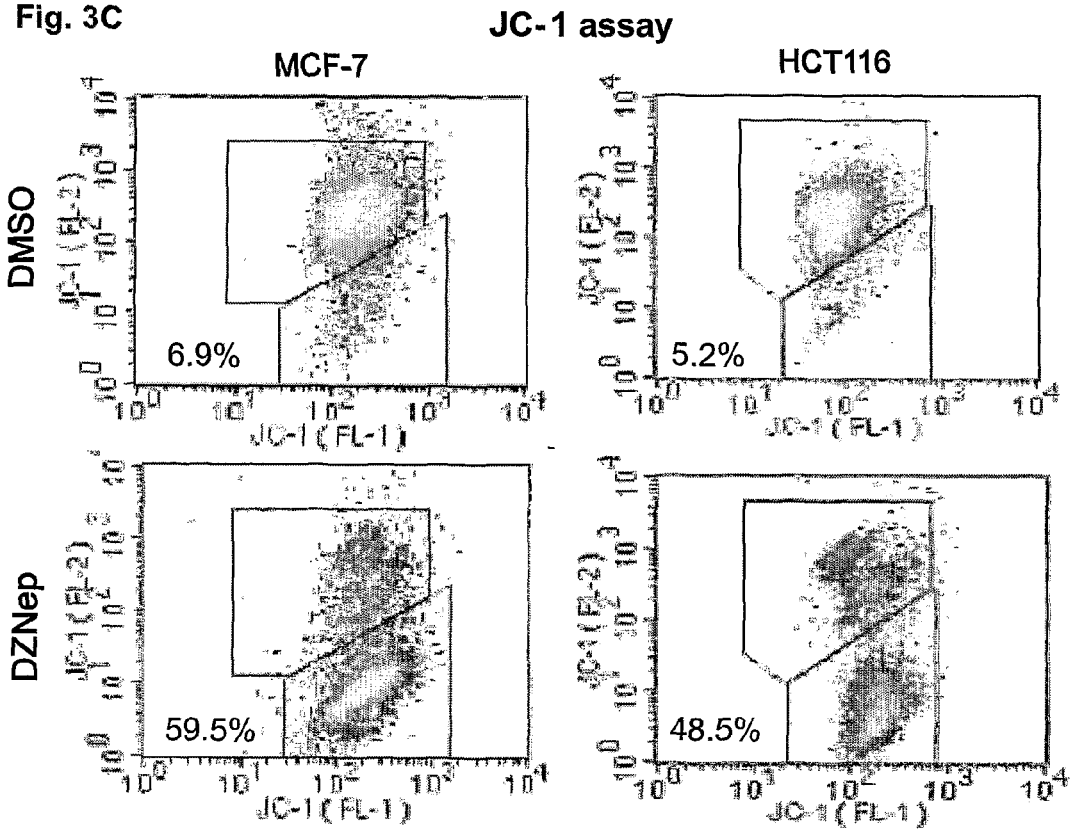
Fig. 3C  JC-1 assay

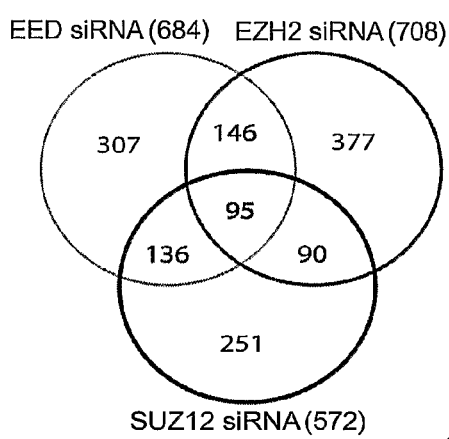
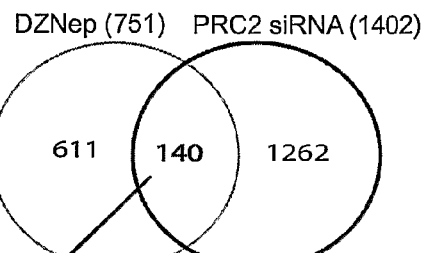
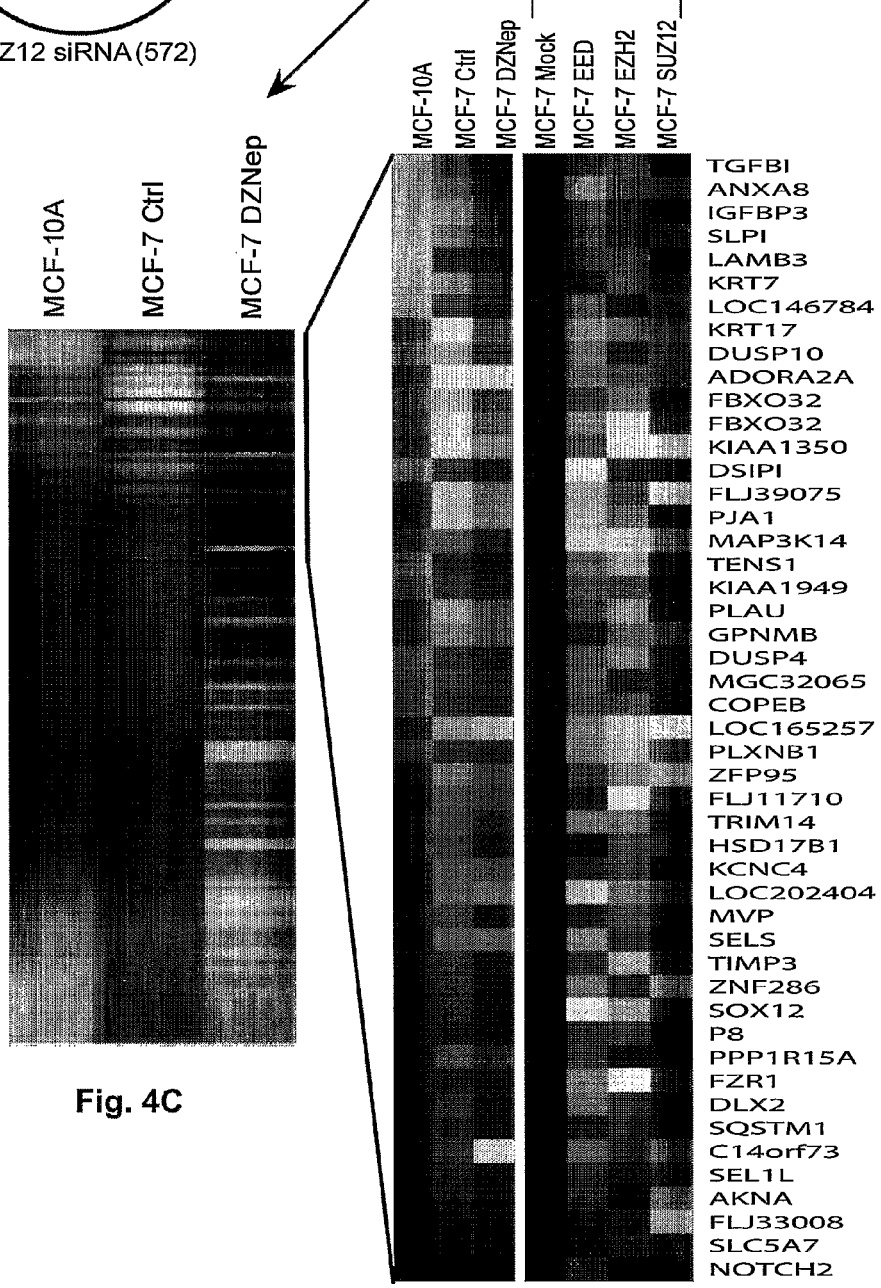
Fig. 4A
Fig. 4B
Fig. 4C

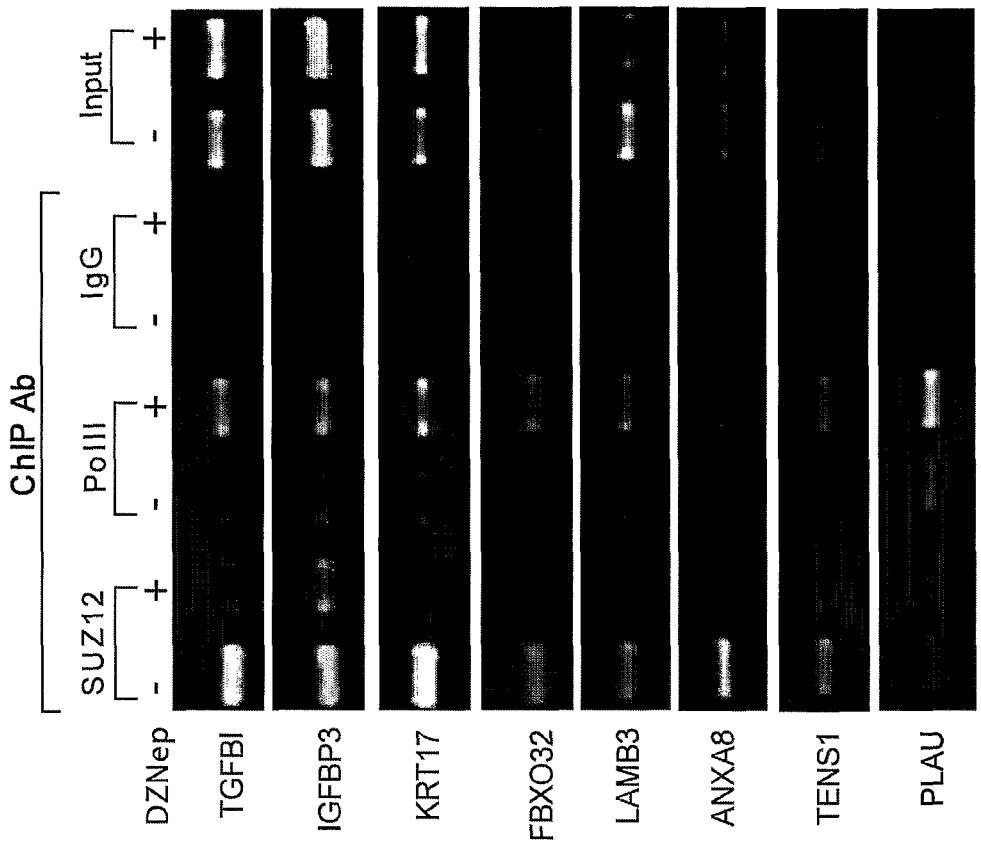
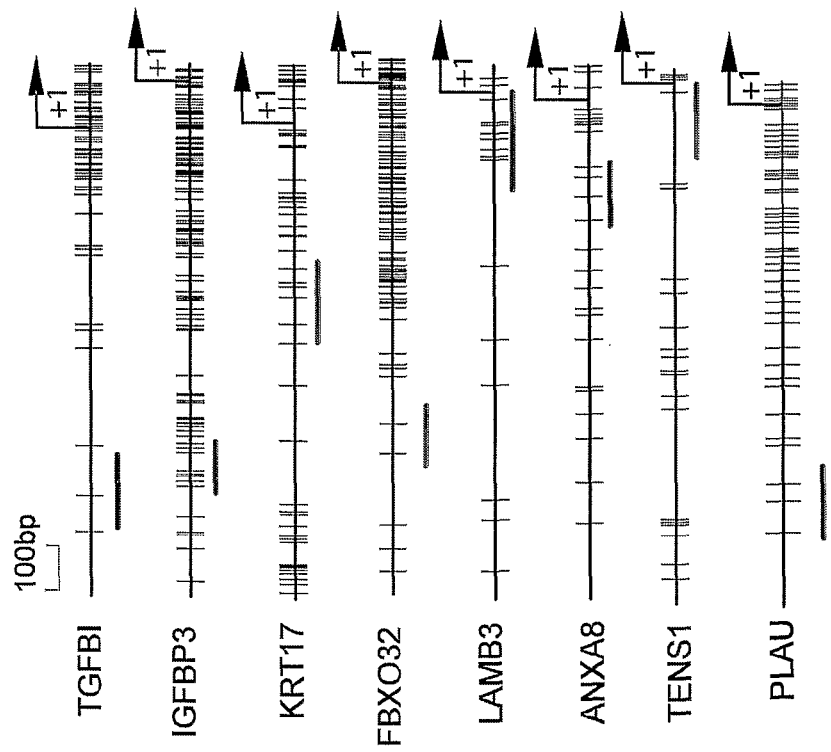
Fig. 5B
Fig. 5A

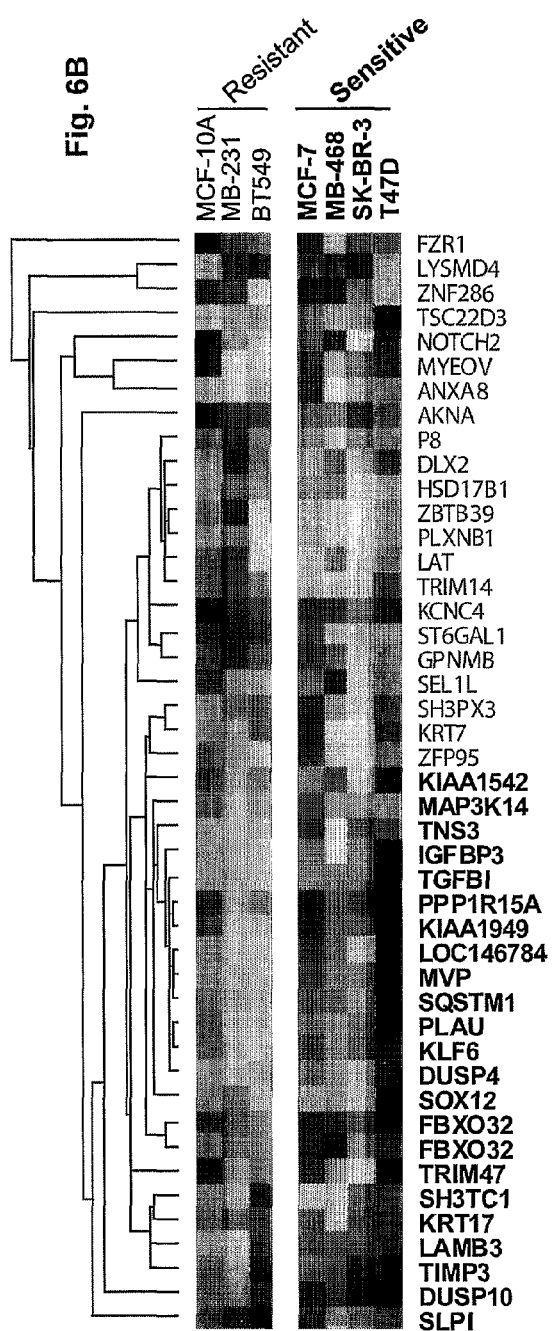
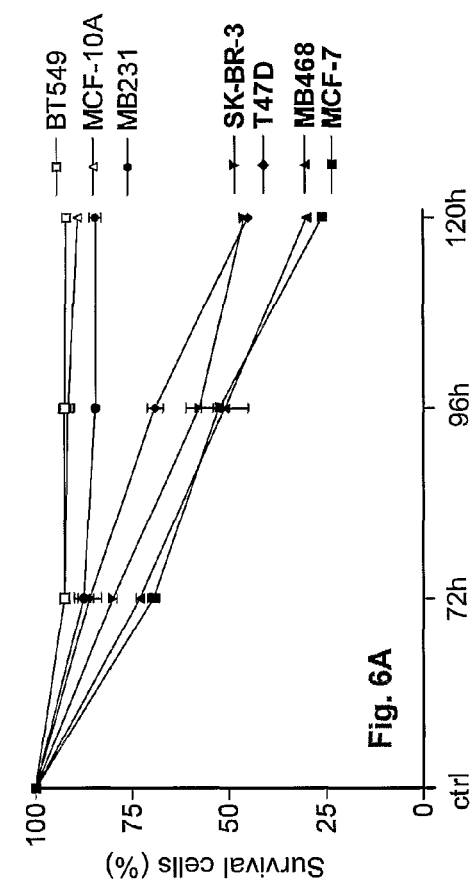
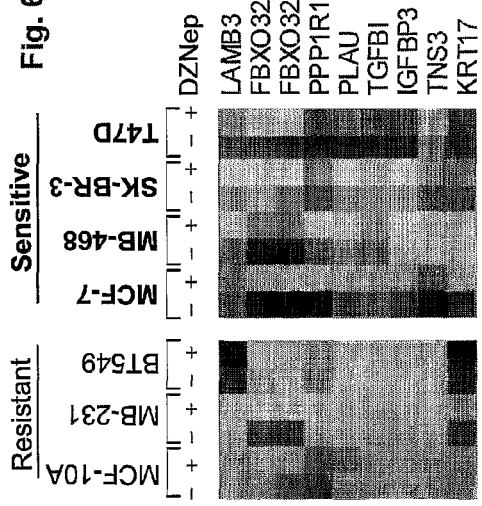

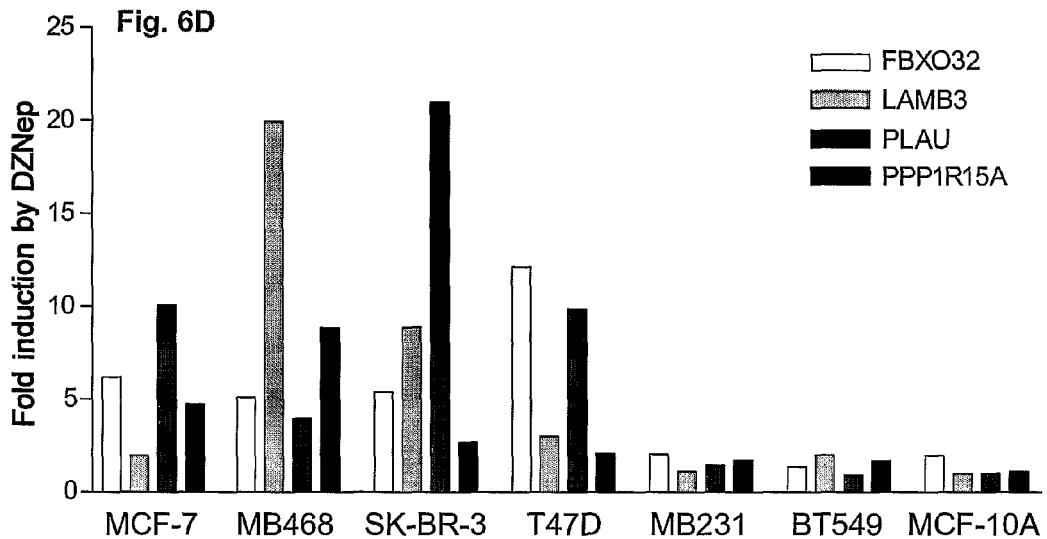
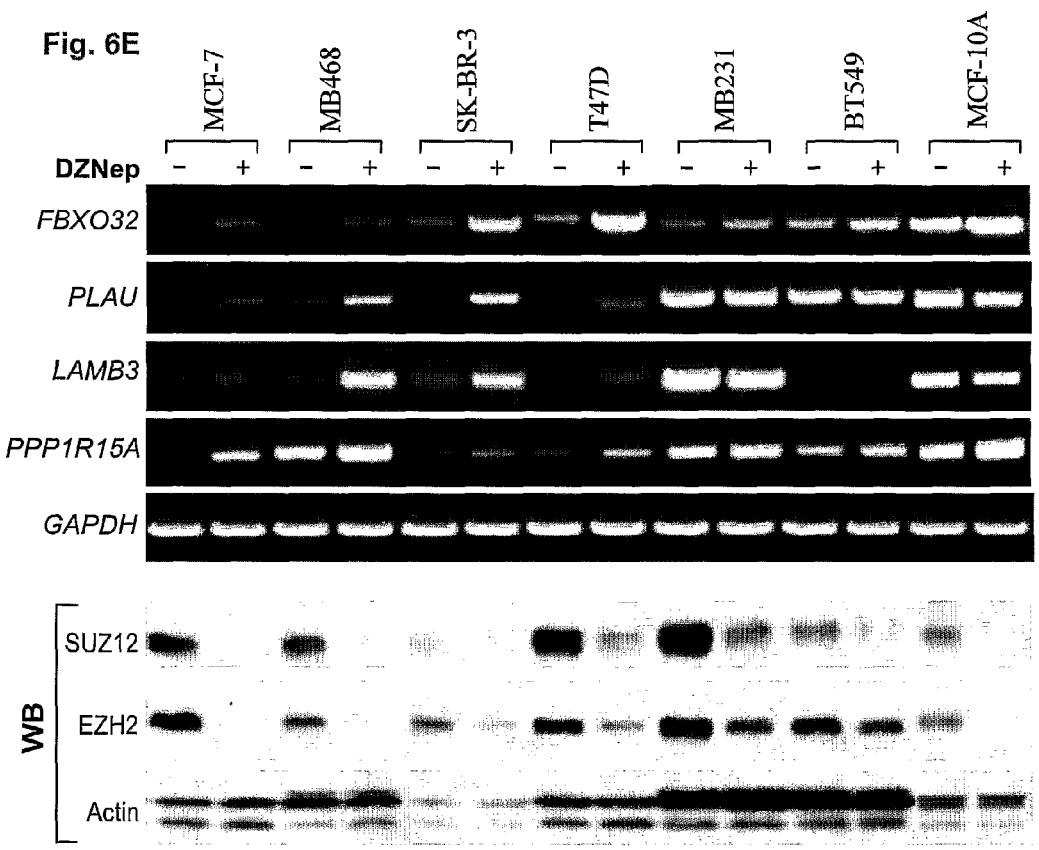

```
                             SEQUENCE LISTING

<160> NUMBER OF SEQ ID NOS: 21

<210> SEQ ID NO 1
<211> LENGTH: 64
<212> TYPE: DNA
<213> ORGANISM: Artificial Sequence
<220> FEATURE:
<223> OTHER INFORMATION: Oligonucleotide for SUZ12 siRNA

<400> SEQUENCE: 1
gatccccgtc gcaacggacc agttaattca agagattaac tggtccgttg cgactttttg      60
gaaa                                                                    64

<210> SEQ ID NO 2
<211> LENGTH: 64
<212> TYPE: DNA
<213> ORGANISM: Artificial Sequence
<220> FEATURE:
<223> OTHER INFORMATION: Oligonucleotide for SUZ12 siRNA

<400> SEQUENCE: 2
tcgatttcca aaaagtcgca acggaccagt tgatctcttg aattaactgg tccgttgcga      60
cggg                                                                    64

<210> SEQ ID NO 3
<211> LENGTH: 21
<212> TYPE: DNA
<213> ORGANISM: Artificial Sequence
<220> FEATURE:
<223> OTHER INFORMATION: Oligonucleotide for EZH2 siRNA

<400> SEQUENCE: 3
aagactctga atgcagttgc t                                                 21

<210> SEQ ID NO 4
<211> LENGTH: 21
<212> TYPE: DNA
<213> ORGANISM: Artificial Sequence
<220> FEATURE:
<223> OTHER INFORMATION: Oligonucleotide for EZH2 siRNA

<400> SEQUENCE: 4
aagcactatg ttggccatgg a                                                 21
```

<210> SEQ ID NO 5
<211> LENGTH: 19
<212> TYPE: DNA
<213> ORGANISM: Artificial Sequence
<220> FEATURE:
<223> OTHER INFORMATION: Target sequence of FBXO32 siRNA

<400> SEQUENCE: 5
gtcacatcct ttcctggaa                                                19

<210> SEQ ID NO 6
<211> LENGTH: 22
<212> TYPE: DNA
<213> ORGANISM: Artificial Sequence
<220> FEATURE:
<223> OTHER INFORMATION: Primer TGFBI

<400> SEQUENCE: 6
atgtcacttg cctccaccca tc                                            22

<210> SEQ ID NO 7
<211> LENGTH: 21
<212> TYPE: DNA
<213> ORGANISM: Artificial Sequence
<220> FEATURE:
<223> OTHER INFORMATION: Primer TGFBI

<400> SEQUENCE: 7
acctgctctg aggcctgaaa g                                             21

<210> SEQ ID NO 8
<211> LENGTH: 21
<212> TYPE: DNA
<213> ORGANISM: Artificial Sequence
<220> FEATURE:
<223> OTHER INFORMATION: Primer IGFBP3

<400> SEQUENCE: 8
ttcacccaag gcttcgtgct g                                             21

<210> SEQ ID NO 9
<211> LENGTH: 20
<212> TYPE: DNA
<213> ORGANISM: Artificial Sequence
<220> FEATURE:
<223> OTHER INFORMATION: Primer IGFBP3

<400> SEQUENCE: 9
tccgcgggag gagactttcc                                               20

<210> SEQ ID NO 10
<211> LENGTH: 23
<212> TYPE: DNA
<213> ORGANISM: Artificial Sequence
<220> FEATURE:
<223> OTHER INFORMATION: Primer KRT17

<400> SEQUENCE: 10
aacccatttc cccaccagac agg                                           23

<210> SEQ ID NO 11
<211> LENGTH: 21
<212> TYPE: DNA
<213> ORGANISM: Artificial Sequence
<220> FEATURE:
<223> OTHER INFORMATION: Primer KRT17

```
<400> SEQUENCE: 11
aaatcctcgt gctgagtgcc g                                              21

<210> SEQ ID NO 12
<211> LENGTH: 21
<212> TYPE: DNA
<213> ORGANISM: Artificial Sequence
<220> FEATURE:
<223> OTHER INFORMATION: Primer FBXO32

<400> SEQUENCE: 12
ttgttgaagg cctgcactgg g                                              21

<210> SEQ ID NO 13
<211> LENGTH: 21
<212> TYPE: DNA
<213> ORGANISM: Artificial Sequence
<220> FEATURE:
<223> OTHER INFORMATION: Primer FBXO32

<400> SEQUENCE: 13
tgatgtaccc agggccaatg c                                              21

<210> SEQ ID NO 14
<211> LENGTH: 20
<212> TYPE: DNA
<213> ORGANISM: Artificial Sequence
<220> FEATURE:
<223> OTHER INFORMATION: Primer LAMB3

<400> SEQUENCE: 14
gcaggtgggc attgtggagc                                                20

<210> SEQ ID NO 15
<211> LENGTH: 21
<212> TYPE: DNA
<213> ORGANISM: Artificial Sequence
<220> FEATURE:
<223> OTHER INFORMATION: Primer LAMB3

<400> SEQUENCE: 15
tccagatcgc ctgaaagctc c                                              21

<210> SEQ ID NO 16
<211> LENGTH: 23
<212> TYPE: DNA
<213> ORGANISM: Artificial Sequence
<220> FEATURE:
<223> OTHER INFORMATION: Primer ANXA8

<400> SEQUENCE: 16
gaatgatgaa aatgggctgg gtg                                            23

<210> SEQ ID NO 17
<211> LENGTH: 23
<212> TYPE: DNA
<213> ORGANISM: Artificial Sequence
<220> FEATURE:
<223> OTHER INFORMATION: Primer ANXA8

<400> SEQUENCE: 17
gaaattctta gctccagcct gcg                                            23

<210> SEQ ID NO 18
<211> LENGTH: 22
```

```
<212> TYPE: DNA
<213> ORGANISM: Artificial Sequence
<220> FEATURE:
<223> OTHER INFORMATION: Primer TENS1

<400> SEQUENCE: 18
tggcctggga gctttcttta cc                                              22

<210> SEQ ID NO 19
<211> LENGTH: 20
<212> TYPE: DNA
<213> ORGANISM: Artificial Sequence
<220> FEATURE:
<223> OTHER INFORMATION: Primer TENS1

<400> SEQUENCE: 19
tctgggccaa cgttgctttg                                                 20

<210> SEQ ID NO 20
<211> LENGTH: 23
<212> TYPE: DNA
<213> ORGANISM: Artificial Sequence
<220> FEATURE:
<223> OTHER INFORMATION: Primer PLAU

<400> SEQUENCE: 20
ggaagcacca acagtttatg ccc                                             23

<210> SEQ ID NO 21
<211> LENGTH: 21
<212> TYPE: DNA
<213> ORGANISM: Artificial Sequence
<220> FEATURE:
<223> OTHER INFORMATION: Primer PLAU

<400> SEQUENCE: 21
atcagagggg gaaaggcaag g                                               21
```

METHODS FOR CANCER THERAPY AND STEM CELL MODULATION

CROSS-REFERENCE TO RELATED APPLICATIONS

The present application claims priority under 35 U.S.C. 371 to International Application No. PCT/SG2006/000350 (published PCT application No. WO 2007/100304), filed Nov. 15, 2006, which claims priority to U.S. Application No. 60/778,532, filed Mar. 2, 2006. The entire contents of each of the above-referenced applications are incorporated herein by reference.

FIELD OF THE INVENTION

The present invention relates to methods, including compounds and compositions, for the treatment and prophylaxis of cancer by inducing apoptosis in a tumour cell. The invention also relates to methods, compounds and compositions for modulating pluripotency and/or self-renewing characteristics of a stem cell/progenitor cell (including a cancer stem cell).

BACKGROUND OF THE INVENTION

Cancer is a major cause of death worldwide, being the second-leading cause of death in developed countries and even the number one cause of death in e.g. Australia, Japan, Korea, Singapore and the male population of the UK and Spain. The number of people who develop cancer each year is increasing.

Increasing evidence points to the important roles of epigenetic alterations in cancer development. These involve DNA hypermethylation as well as chromatin modifications such as histone methylation and deacetylation (for a review see Feinberg, A. P., et al., Nature Reviews Genetics (2005) 7, 21-33). Many tumour suppressor genes have been found to be silenced by epigenetic mechanisms. Unlike genes harbouring disabling genetic mutations, tumour suppressor genes epigenetically silenced can be reactivated and to cause cells to go into apoptosis or senescence. This feature makes epigenetic modifications an ideal target for therapeutic interventions in cancer. It has been shown that specific inhibitors of DNA methylation, 5-azacytidine, and its deoxy analogue, 5-aza-2'-deoxycytidine can inhibit the DNA-dependent methyltransferase (DNMT) activity, reverse the silencing of tumour suppressor genes and have shown utility for the treatment of haematological malignancies. Clinical trials are also underway for agents that interfere with enzymes that modify histone, such as histone deacetylase inhibitors.

Similar epigenetic alterations such as DNA methylation and histone modifications appear to be involved in the maintenance, proliferation and differentiation of stem cells. Mature cells of the various tissues of an organism arise from progenitor cells, which possess a broad developmental potential and replicative capacity. Peripheral blood for example contains progenitor cells that can differentiate into endothelial or vascular smooth muscle cells. Progenitor cells in turn originate from stem cells, which have also been identified in most tissues. Stem cells are fully undifferentiated cells that are able to differentiate into any mature functional cells, such as heart, liver, brain cells etc., while retaining the ability to proliferate indefinitely. Methylation and demethylation of DNA are known to regulate transcriptional states during germ cell development, between fertilisation and blastocyst formation, and early development in mammals (for a review see e.g. Santos, F., and Dean, W., Reproduction (2004) 127, 643-651).

Evidence for a role of epigenetic alterations in the maintenance of stem cells is for instance the observation that late passages of embryonic stem cell cultures show a variety of clonal DNA alterations, such as a differential methylation of inter alia the promoter region of the putative tumour suppressor gene RASSF1 (Maitra et al., Nature Genetics (2005) 37, 10, 1099-1103). Epigenetic disruption of progenitor cells has furthermore been suggested to be a key determinant of cancer progression (Feinberg, A. P., et al., 2005, supra).

Currently, cancer therapy involves surgery or focuses on the functional or genetic changes associated with the transformation of cells into malignant cells. An ideal anti-cancer drug should selectively kill, or at least inhibit, rapidly proliferating cancerous cells, while leaving non-cancerous cells unaffected. Recent approaches include immunotherapy using antibodies directed to markers of selected types of cancer cells (e.g. US patent application 2005/0244417), the application of agonists to receptors that are expressed on certain types of cancer cells (US patent application 2006/0147456), the application of interferon-containing chitosan-lipid particles (US patent application 2005/0266093), as well as the application of a compound that acts as a cytotoxic agent for a certain type of prostate cancer cells by an unknown mechanism (US patent application 2005/0245559).

In recent years research efforts have also been undertaken to develop an epigenetic cancer therapy, since abnormal patterns of DNA methylation in cancer cells are known for more than 20 years (for an overview see e.g. Brown, R. and Strathdee, G., Trends in Molecular Medicine (2002) 8, 4 (Suppl.), S43-S48, or Yoo, C. B. and Jones, P. A., Nature Reviews Drug Discovery (2006) 5, 1, 37-50). Nevertheless only two DNA methyl-transferase inhibitors, 5-azacytidine (Vidaza™) and decitabine (Dacogen™) have made it to the market. They have been approved for the treatment of myelodysplastic syndrome, a haematological condition also known as "preleukemia". There is therefore still a need in the art for novel compounds and compositions for treating or preventing cancer or neoplastic disease that preferentially kill rapidly cancerous cells.

With respect to the modulation of stem cells, the ability of embryonic stem cells to readily differentiate continues to pose a major practical challenge. In order to maintain embryonic stem cells in a pluripotent state, their differentiating during handling and growing in culture has to be prevented. For this reason they are traditionally cultured in the presence of fetal calf serum on a layer of feeder cells (see e.g. U.S. Pat. No. 5,843,780 and U.S. Pat. No. 6,090,622) or in fibroblast-conditioned medium (CM). Nevertheless, even under carefully controlled conditions embryonic stem cells may undergo spontaneous differentiation during in-vitro propagation. Leukaemia inhibitory factor, a factor mediating self-renewal in mouse embryonic stem cells, has also been found to inhibit differentiation of mouse embryonic stem cells, but it does not replace the role of feeder cells in preventing differentiation of human embryonic stem cells. Therefore, means of maintaining pluripotency and/or self-renewing characteristics of embryonic stem cells would be a substantial achievement towards realizing the full commercial potential of stem cell therapy.

Stem cells are also found in carcinomas called teratoma of various tissues (often of the testes and the ovary) that produce tissues consisting of a mixture of two or more embryological layers. The malignant forms of such carcinomas are also called teratocarcinoma. Development of stem cells in murine teratocarcinoma parallels events in the normal embryo. Their presence can explain that chemotherapy often removes the bulk of a tumour mass without preventing tumour recurrence (Chambers, I. Smith, A, *Oncogene* (2004), 23, 7150-7160). Furthermore, stem cells have been suggested to be a source of cancer cells in solid tumours, including breast and brain cancer. Leukaemias have been shown to be generated by a limited number of leukaemia stem cells of heterogeneous origin (Passegue, E. et al., *Proc. Natl. Acad. Sci. USA* (2003), 100, 11842-11849). Therefore, means of abrogating pluripotency and/or self-renewing characteristics of stem cells in such tumours would typically be a precondition for a permanent removal of such carcinomas.

Accordingly it is an object of the present invention to provide a method, as well as compounds and compositions that are capable of preferentially killing a cancer cell without affecting a non-cancerous cell. It is a further object of the present invention to provide a method of modulating pluripotency and/or self-renewing characteristics of a stem/progenitor cell.

SUMMARY OF THE INVENTION

In one aspect the present invention relates to the use of a compound in the manufacture of a medicament for inducing apoptosis in a tumour cell and/or modulating pluripotency and/or self-renewing characteristics of a stem/progenitor cell. The compound is of the general formula (I)

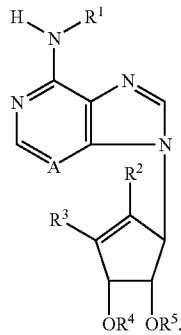

In formula (I) A is C or N. $R^1$, $R^4$ and $R^5$ are independently selected from the group consisting of H and aliphatic, cycloaliphatic, aromatic, arylaliphatic, and arylcycloaliphatic hydrocarbyl groups, comprising 0-3 heteroatoms selected from the group consisting of N, O, S, and Si. $R^4$ and $R^5$ may optionally be linked so as to define an aliphatic hydrocarbyl bridge. $R^2$ is selected from the group consisting of H and a halogen (F, Cl, Br or I). $R^3$ is H, or an aliphatic or arylaliphatic hydrocarbyl group comprising 1-8 main chain carbon atoms and 0-3 heteroatoms selected from the group consisting of N, O, S, Si, and halogen (Cl, F, Br, I). In some embodiments, $R^2$ is F or Cl. In some embodiments, also $R^3$ (independently or at the same time as $R^2$) can also be F or Cl.

In another aspect the present invention provides a method of inducing apoptosis in a tumour cell as well as a method of modulating pluripotency and/or self-renewing characteristics of a stem/progenitor cell. The methods include administering to the respective cell a compound as defined above.

In yet another aspect the present invention provides a pharmaceutical composition for inducing apoptosis in a tumour cell and/or modulating pluripotency and/or self-renewing characteristics of a stem/progenitor cell. The pharmaceutical composition includes a compound as defined above or a pharmaceutically acceptable salt thereof. The pharmaceutical composition may further include a carrier or diluent.

In yet another aspect the present invention provides a method for modulating gene expression in a cell. The respective cell expresses the components of a polycomb repressive complex. The method includes administering to said cell a compound of the general formula (I) (see above).

BRIEF DESCRIPTION OF THE DRAWINGS

The invention will be better understood with reference to the detailed description when considered in conjunction with non-limiting examples and the accompanying drawings, in which.

1; O: 5-(6-amino-2-fluoro-9H-purin-9-yl)-3-(hydroxymethyl)-3-cyclopentene-1,2-diol, CAS-No. (hydrochloride) 138660-07-8; P: 5-(6-amino-8-chloro-9H-purin-9-yl)-4-chloro-3-cyclopentene-1,2-diol, CAS-No. 127828-72-2; Q: 3-(6-amino-9H-purin-9-yl)-4,5-dihydroxy-1-cyclopentene-1-carboxylic acid, CAS-No. 179929-29-4; R: 5-(6-amino-9H-purin-9-yl)-3-propyl-3-cyclopentene-1,2-diol, CAS-No. 851071-49-3; S: 5-(6-amino-9H-purin-9-yl)-3-(fluoromethyl)-3-cyclopentene-1,2-diol, CAS-No. 303964-14-9; T: 5-(6-amino-9H-purin-9-yl)-4-fluoro-3-(fluoromethyl)-3-cyclopentene-1,2-diol, CAS-No. 805245-51-6; U: 5-(6-amino-9H-purin-9-yl)-4-fluoro-3-(mercaptomethyl)-3-cyclopentene-1,2-diol, CAS-No. 805245-54-9; V: 5-(6-amino-9H-purin-9-yl)-3-(1-hydroxy-2-propynyl)-3-cyclopentene-1,2-diol, CAS-No. 141794-36-7.

Figure 3A:
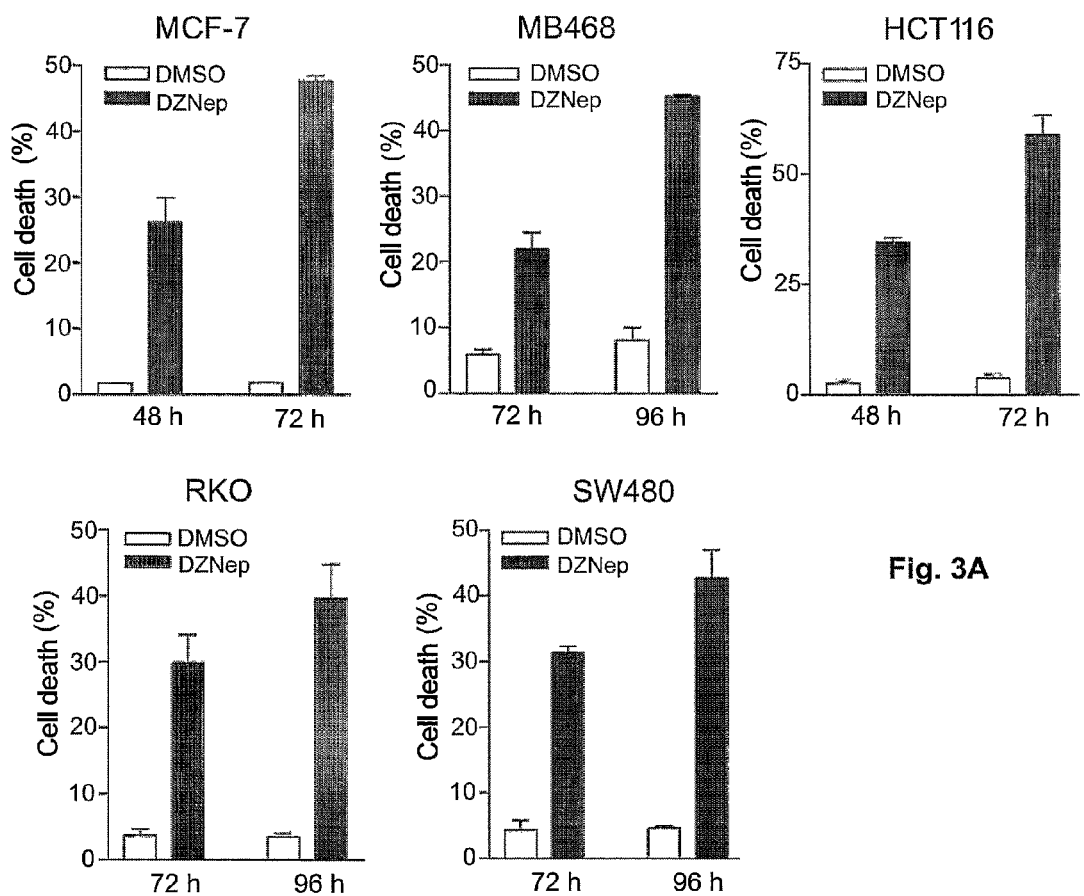

FIG. 3A depicts the detection of cell death of a variety of cancer cells upon exposure to 3-deazaneplanocin (DZNep) compared to untreated controls cells (DMSO=dimethyl sulfoxide). Breast cancer MCF-7 and MB-468 cells, colorectal HCT116, RKO and SW480 cells were treated with 5 μm 3-deazaneplanocin for 48 and 72 h, and cell death was detected by means of propodium iodide (PI) staining and flow cytometry analysis. Shown is the average of three independent experiments.

FIG. 3B depicts the detection of mitochondrial membrane potential of HCT116 cells by staining with the dye 5,5',6,6'-tetrachloro-1,1',3,3'-tetraethyl-benzamidazolocarbocyanin iodide (JC-1). Exposure of cells to 3-deazaneplanocin (DZNep) resulted in loss of mitochondrial membrane potential (right hand side), indicating apoptosis.

FIG. 3C compares the apoptosis in HCT116 cells (right hand side, data of FIG. 3B) to the apoptosis in MCF-7 cells (left hand side).

Figure 3D:
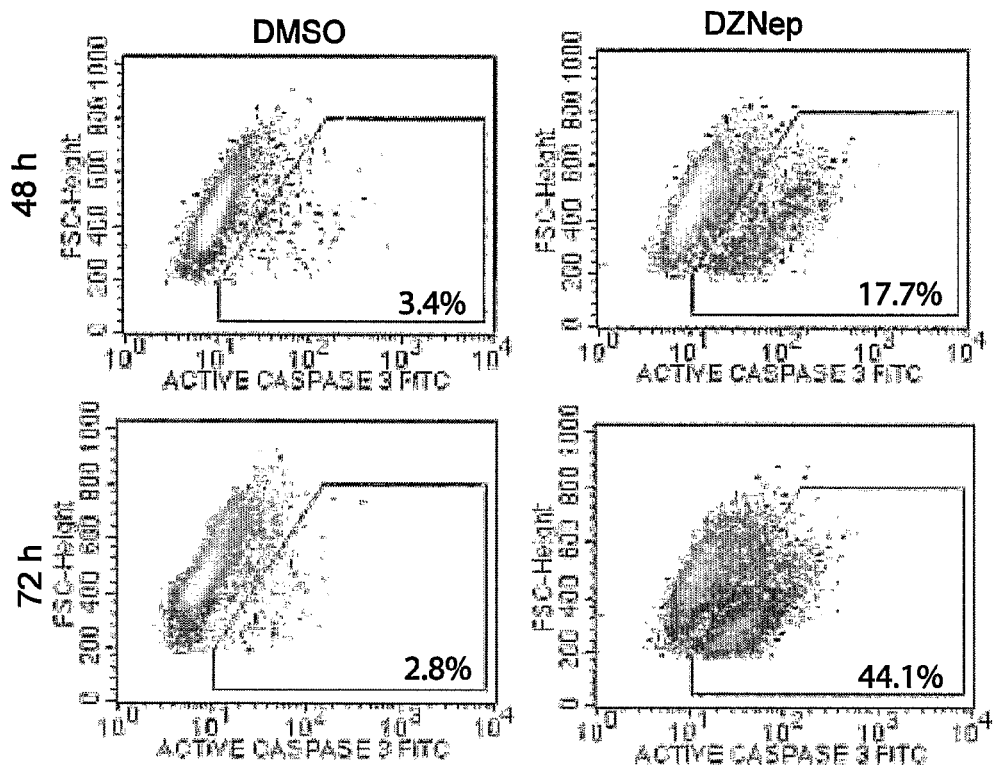

FIG. 3D depicts the detection of activation the protease caspase 3 potential in HCT116 cells by 3-deazaneplanocin (DZNep, right hand side), which occurs during apoptosis.

Figure 3E:
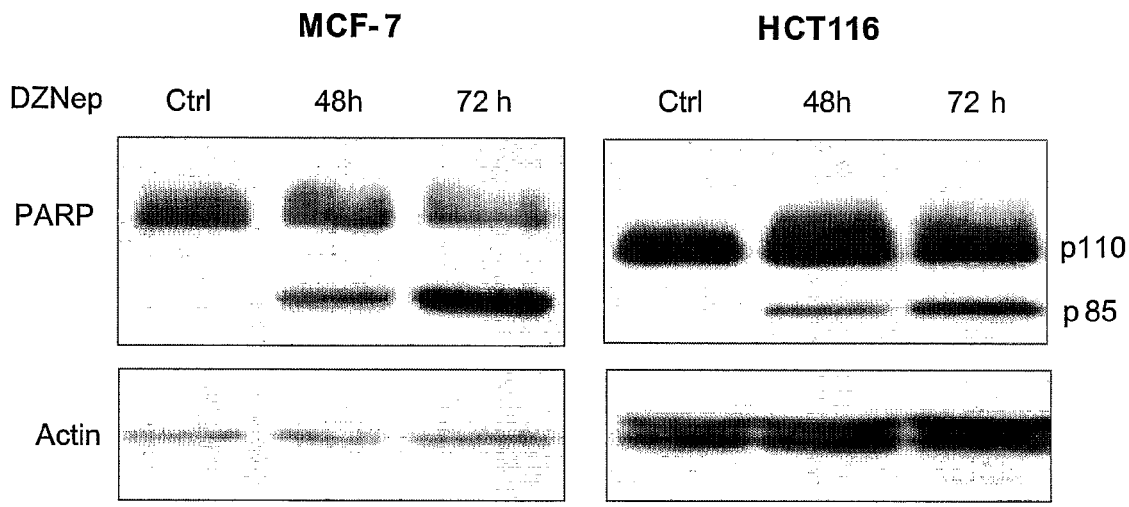

FIG. 3E depicts a Western blot analysis of the activation of caspases. MCF-7 and HCT16 cells were treated with 5 μM 3-deazaneplanocin ("DZNep") for 48 and 72 h before analysis of whole-cell extracts. Activation of caspases and poly (ADP-ribose) polymerase ("PARP") was detected after 3-deazaneplanocin treatment. β-Actin ("Actin") was used as a loading control.

Figure 3F:
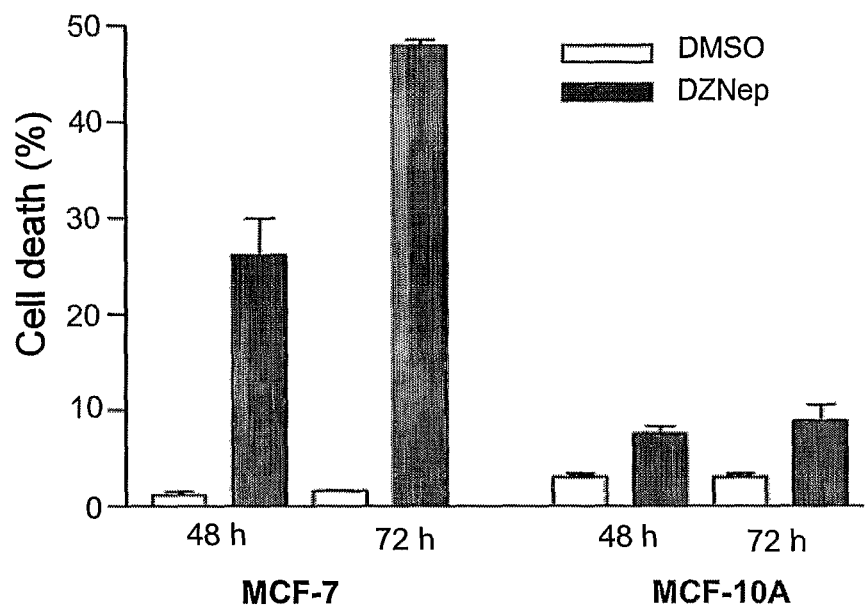

FIG. 3F shows a plot of FACS analysis data, comparing apoptosis of MCF-7 and non-cancerous breast epithelial MCF10A cells. Cells were treated with 5 μM 3-deazaneplanocin (DZNep, dark bars) for indicated times. While 3-deazaneplanocin treatment resulted in a progressive and marked apoptosis in MCF-7 cells, no obvious apoptosis was induced in MCF10A cells.

Figure 3G:
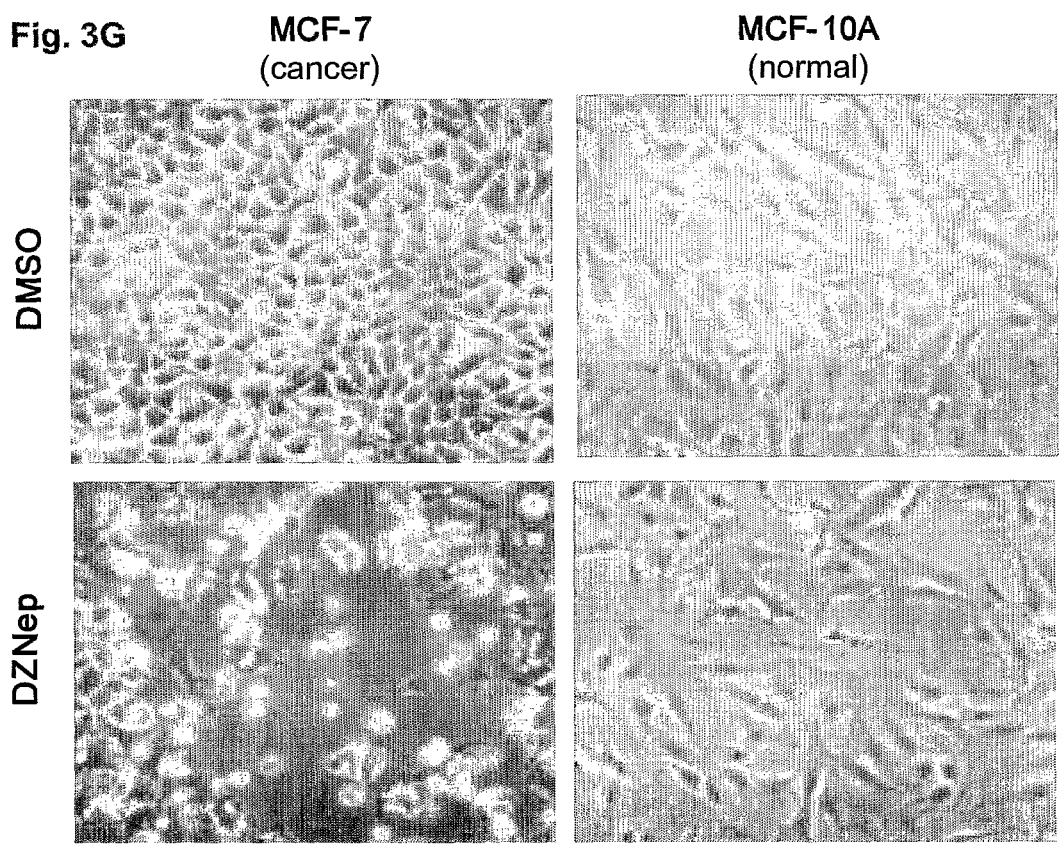

FIG. 3G shows a comparison of the effect of 3-deazaneplanocin (DZNep) on breast cancer MCF-7 cells and non-cancerous MCF-10A breast epithelial cells. 3-deazaneplanocin-induced cell death was only marginal in MCF10A cells, while significant morphological changes were detected in MCF-7 cells.

Figure 3H:
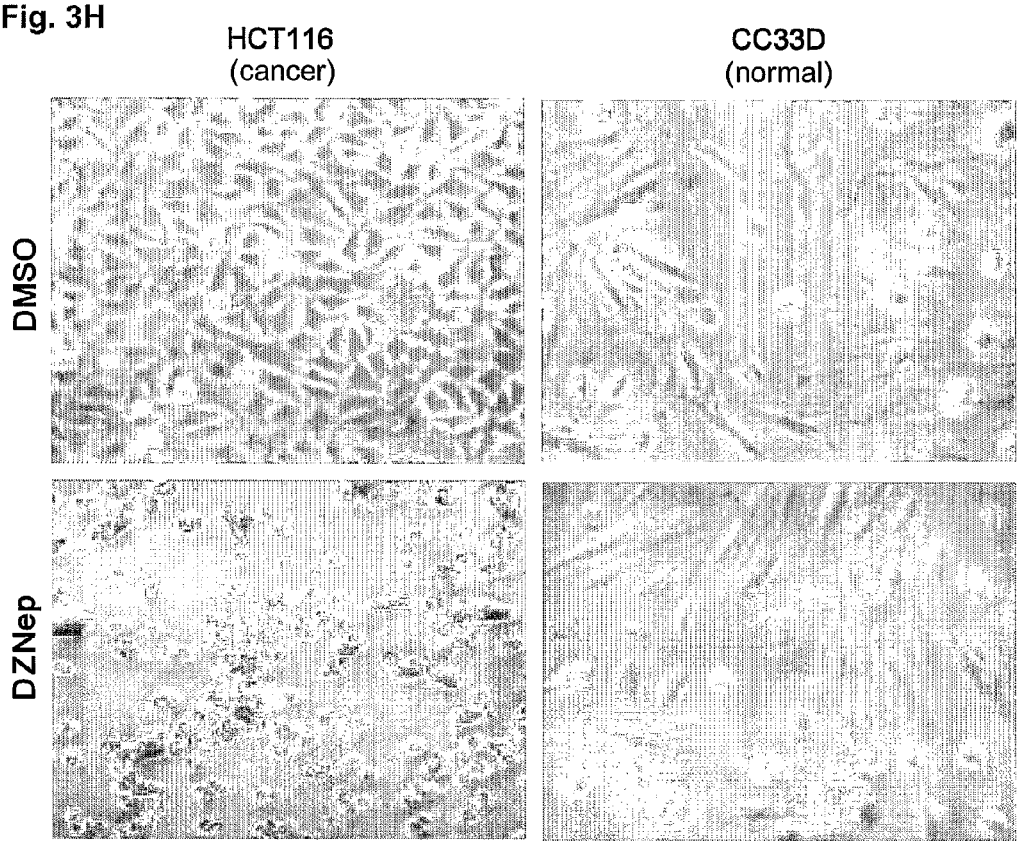

FIG. 3H shows a comparison of the effect of 3-deazaneplanocin on colorectal HCT116 cells, compared to CC33D primary colon epithelial cells. Again, 3-deazaneplanocin induced significant morphological changes in HCT116 cells, while hardly any cell death was observed in CC33D cells.

Figure 3I:
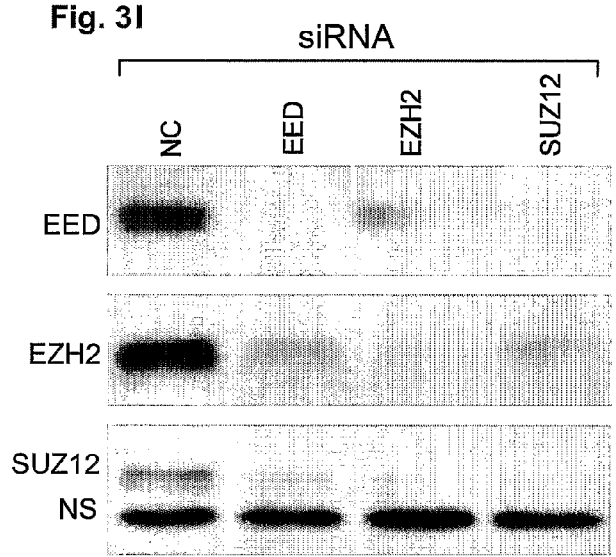

FIG. 3I depicts Western blot analysis of the depletion of the individual PRC2 proteins EED, EZH2, and SUZ12 in MCF-7 cells by small interfering RNA (siRNA), 48 h after transfection. A non-specific (NS) signal is present in all samples.

Figure 3J:
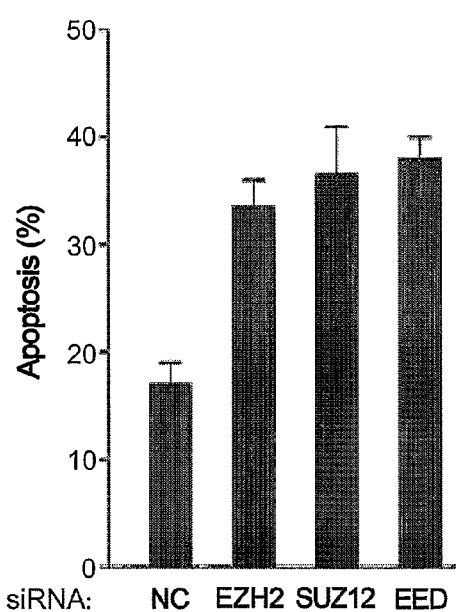

FIG. 3J depicts the detection of apoptosis in MCF-7 cells, in which one of the PRC2 proteins EED, EZH2, and SUZ12 was depleted by means of siRNA (cf. FIG. 3E). Cell death was measured by PI staining and FACS analysis. Substantial apoptosis-induction was observed following knock-out of each of the respective proteins.

FIG. 4 illustrates schematically the identification of PRC2 targets repressed in breast cancer and activated by 3-deazaneplanocin. Proteins EZH2, SUZ12 and EED were knocked down individually by means of siRNA. Using the Illumina Gene Expression BeadChip, genes that were upregulated ≧2-fold were identified and checked for overlaps (FIG. 4A). 1402 genes were found to be upregulated, of which 95 genes were upregulated by all the three siRNA treatments. Treatment of MCF-7 cells with DZNep for 72 h led to the identification of 750 genes up-regulated by at least 2-fold, of which 140 genes were found to be candidate PRC2 target genes (FIG. 4B). Expression profiles of these 140 genes in MCF-7 cells and MCF10A cells were analysed by gene cluster analysis to determine candidate PRC2 targets specifically repressed in breast cancer (FIG. 4C). A cluster of 45 genes was identified with an expression of at least two-fold lower in MCF-7 cells compared to MCF10A cells. The rest of the putative PRC2 target genes either were expressed in similar levels between the two cell types or even expressed in higher levels in MCF-7 cells (FIG. 4C, left panel). 3-Deazaneplanocin (DZNep) treatment or siRNA knockdown of PRC2 proteins resulted in their re-expression in MCF-7 cells (FIG. 4C, right panel). Semi-quantitative RT-PCR of 10 randomly selected genes form the 47-gene set (FIG. 4D) showed that in each case the candidate gene was highly expressed in MCF10A was undetectable in MCF-7 cells. 3-Deazaneplanocin (DZNep) treatment or siRNA depletion of the PRC2 proteins resulted in their re-expression in MCF-7 cells. Gene ontology (GO) analysis (FIG. 4E) showed that a substantial number of these genes play a role in growth inhibition or apoptosis, such as TGFBI and IGFBP3. This is in striking contrast to MCF10A cells where these 47 PRC2 target genes were already expressed at high levels (FIG. 4E, upper panel) and did not undergo further induction (FIG. 4E, lower panel). Gene expression analysis on a data set consisting of a collection of 28 primary breast tumour samples and 9 normal breast tissues, which included the 47 cancer-specific PRC2-repressed genes, showed that this subset of PRC2 targets are the clinically relevant ones repressed in primary human breast cancers (FIG. 4F). 34 unique probes present in this Affymetrix array data set clearly separated the tumour and normal samples (FIG. 4G). Hierarchical clustering of PRC2 target genes in primary breast tumours (T) and normal breast tissues (N) is indicated in FIG. 4G. I, II and III represent the subsets of genes showing distinct expression patterns. A subset of 17 genes (Cluster I) show lower expression in breast tumours relative to the normal breast tissues, which, as expected, was correlated with the higher EZH2 and SUZ12 expression.

FIG. 5A depicts a schematic representation of 5' regions of the 8 candidate PRC2 target genes. Arrows point to the transcription start sites. Vertical bars indicate CpG sites. Regions analysed by PCR are shown by black bars on the bottom. ChIP PCR primers were designed to be located on the core promoter regions of the analysed genes.

FIG. 5B depicts the analysis of PRC2 binding to the top candidate PRC2 target gene promoters by chromatin immunoprecipitation (ChIP). Using SUZ12 and RNA Pol II antibodies, untreated cells displayed a strong binding of SUZ12 to the selected top PRC2 target gene promoters, while only background or minimal binding was detected in non-specific IgG or RNA Pol II pull-down samples. Treatment with 3-deazaneplanocin (+) markedly reduced binding of SUZ12 to these promoters, whereas binding of RNA Pol II was increased. Only background or minimal binding was detected in non-specific IgG or RNA Pol II pull-down samples.

Figure 5C:
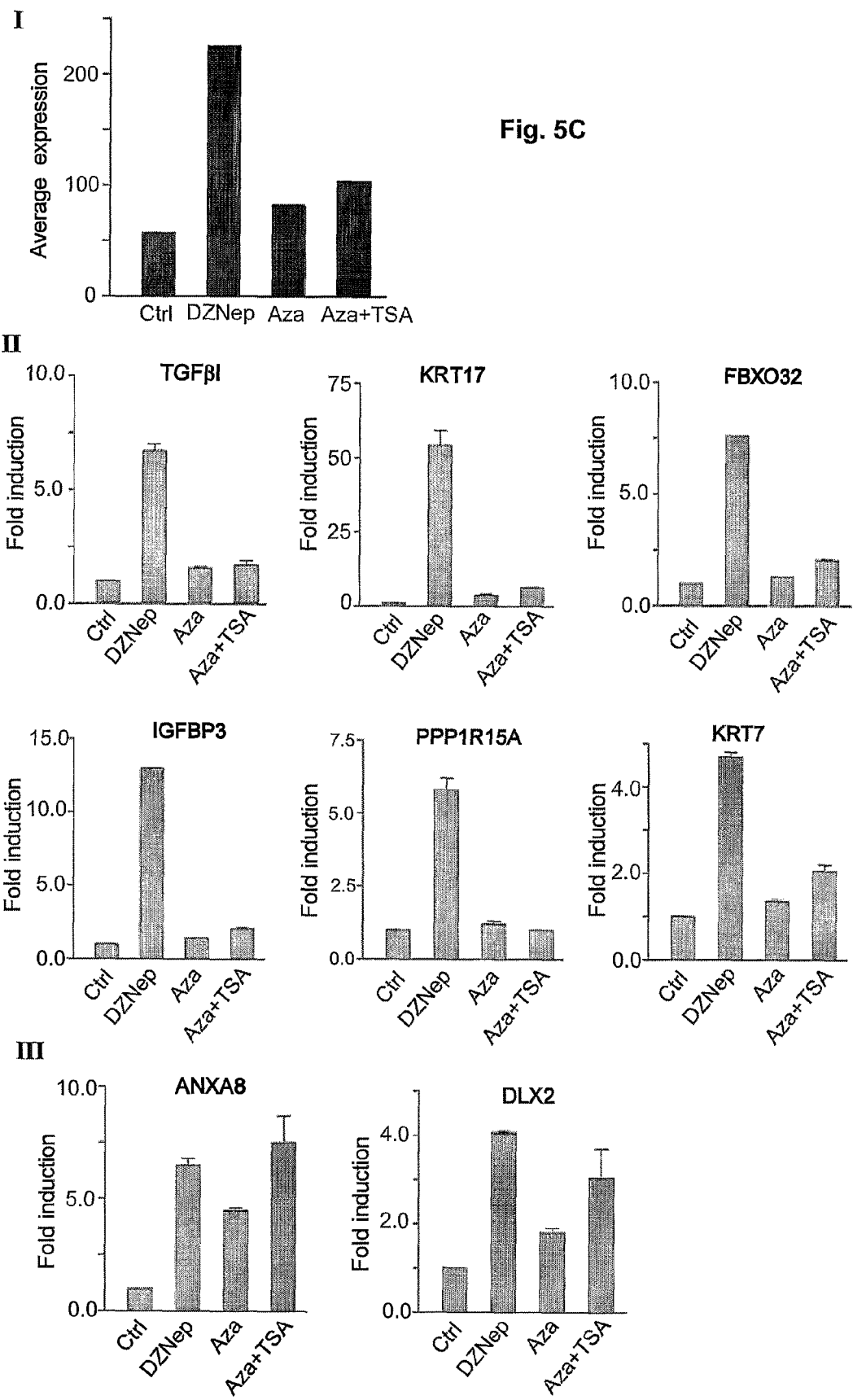

FIG. 5C depicts the effects of 3-deazaneplanocin, 5-azacytidine and the histone deacetylase inhibitor trichostatin A on PRC2 target gene expression. I: MCF-7 cells were untreated or treated with 3-deazaneplanocin (DZNep), 5-azacytidine (5-AzaC) or a combination of 5-azacytidine and trichostatin A (AZA+TSA), and RNA was isolated for gene expression analysis. The averaged expression levels of 140 PRC2 targets are shown. Treatment with 5-azacytidine alone or in combination with trichostatin A did not result in a significant reactivation of the PRC2 targets in general when compared to 3-deazaneplanocin treatment. II: PRC2 targets TGFβI, KRT17 and FBXO32 were activated by 3-deazaneplanocin but not by 5-azacytidine alone or in combination with trichostatin A, as measured by real-time PCR and normalized using 18S rRNA expression. III: PRC2 targets ANXA8 and DLX2 were however activated by both 3-deazaneplanocin and 5-azacytidine alone or in combination with trichostatin A, as measured by real-time PCR and normalized using 18S rRNA expression. These data show that the reactivation of PRC2 target genes by 3-deazaneplanocin was not based on a general DNA hypomethylation. They further show that only for certain PRC2 target genes such as ANXA8 and DLX2 such hypomethylation may occur. For these genes, PRC2 might recruit DNA methyl-transferases to their promoters and coordinately suppress their expression, as suggested by a recent study (Viré, E., et al., Nature (2006), 439, 16, 871-874).

FIG. 6A depicts an analysis of the breast cancer cell lines MCF-7, MB-468, SK-BR-3, MB-231, T47D and BT549 for an apoptotic effect of 5 μM 3-deazaneplanocin over a time frame of 120 hours. Cell death was measured by FACS analysis. Data presented are the average of three independent experiments. MCF-7 cells, MB-468, SK-BR-3 and T47D cells were highly sensitive to 3-deazaneplanocin, whereas MB-231, BT549, together with MCF10A, were not affected by, or highly resistant to, treatment therewith.

FIG. 6B depicts the results of array analysis in these breast cancer cell lines (MCF-7, MB-468, SK-BR-3 and T47D sensitive /MCF10A, MB-231, BT549 resistant) before and after 3-deazaneplanocin treatment. Gene clustering analysis of 45 PRC2 targets revealed that a subset of PRC2 targets (22 genes) were expressed in consistent high levels in resistant cell lines (MCF10A, MB-231, and BT549), but were expressed in lower levels in sensitive cell lines (MCF-7, MB-468, SK-BR-3 and T47D) expressions in indicated breast caner cell lines. Genes marked in bold are highly expressed in resistant cell lines relative to sensitive cell lines.

FIG. 6C depicts genes up-regulated by 3-deazaneplanocin in at least three sensitive cell lines. Among the genes analysed in FIG. 6B the four genes FBXO32, LAMB3, PLAU, and PPP1R15A were found to be commonly induced by DZNep in all four sensitive cell lines. Four additional genes (TGFBI, IGFBP3, TNS3 and KRT17) were induced in 3 out 4 sensitive cell lines. These genes were already highly expressed (except LAMB3 in BT549) in resistant cell lines (MCF10A, MB-231, and BT549) and did not undergo marked further induction after 3-deazaneplanocin treatment FIG. 6D depicts the analysis of expression levels of the validated PRC2 targets in MCF-7, MB-468, SK-BR-3 T47D, MB-231, BT549 cells before and after exposure to 3-deazaneplanocin (DZNep) by quantitative RT-PCR. In breast cancer cell lines MCF-7, MB-468, SK-BR-3, T47D, the expression of genes FBXO32, LAMB3, PLAU, PPP1R15A was activated by 3-deazaneplanocin.

FIG. 6E depicts the analysis of expression levels of the validated PRC2 targets FBXO32, LAMB3, PLAU, and PPP1r15p by conventional RT-PCR (top). Cells were treated as in C. Again, the expression of FBX032, LAMB3, PLAU, PPP1R15A was repressed but reactivated by 3-deazaneplanocin (DZNep) in sensitive breast cancer cell lines (MCF-7, MB-468, SK-BR-3, T47D). The EZH2 and SUZ12 protein levels were determined by Western blotting (bottom). As can be seen, MB-231 cells that seemed to express a higher level of EZH2 protein, many PRC2 targets (top) were nevertheless not suppressed. Expression levels of the PRC2 targets are thus not always reflected by the respective levels of PRC2 proteins, indicating the involvement of additional factors such as DNA methyl-transferases and histone deacetylases.

Figure 6F:
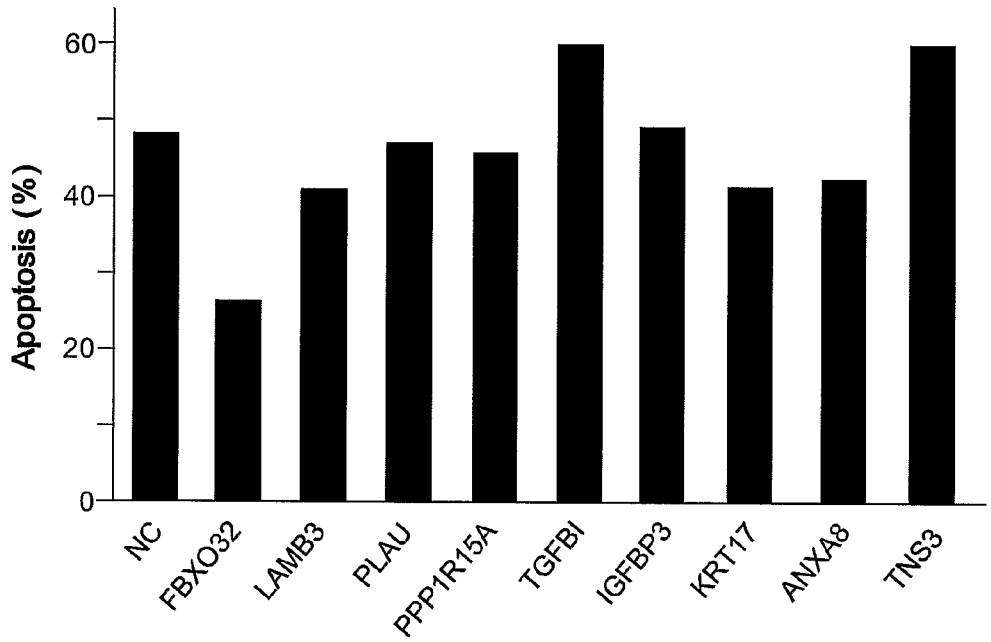

FIG. 6F depicts the effect of depletion of PRC2 targets in MCF-7 cells by siRNA on apoptosis induction by 3-deazaneplanocin, compared to a non-targeting siRNA control (NC). Each of the indicated siRNAs was transfected into MCF-7 cells for 24 h, followed by 5 μM 3-deazaneplanocin treatment for 72 h. Apoptosis was measured by FACS analysis. Only FBXO32 siRNA was capable of reducing the apoptotic response to 3-deazaneplanocin.

Figure 6G:
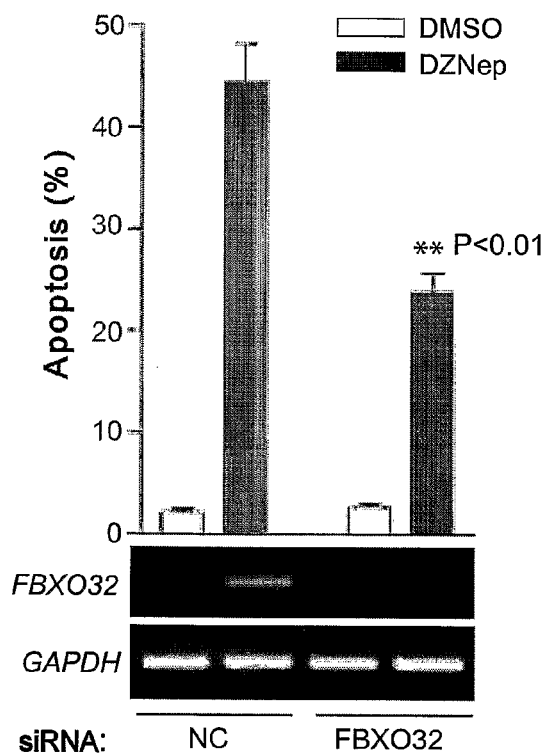

FIG. 6G shows the analysis of the effect of FBXO32 (see FIG. 6F) using a different FBXO32 siRNA. FBXO32 siRNA treatment inhibited 3-deazaneplanocin (DZNep)-induced apoptosis in MCF-7 cells compared to a non-targeting siRNA control (NC). Shown are the results of three independent experiments. The results confirmed that inhibition of FBXO32 induction resulted in significant attenuation of apoptosis induction by 3-deazaneplanocin.

Figure 6H:
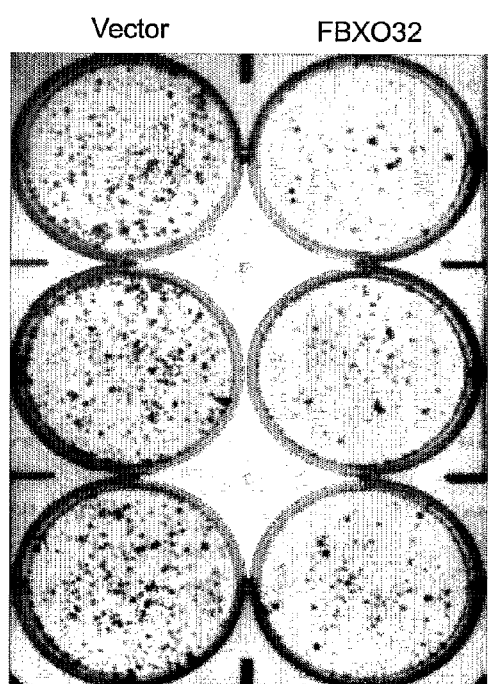

FIG. 6H shows the ability of FBXO32 to affect colony formation. MCF-7 cells were transfected with the plasmid encoding FBXO32 or an empty vector. Cells were selected and assayed for clonogenic survival in triplicates. Transfection of FBXO32 caused a substantial reduction in the number of colonies formed compared to cells transfected with a control vector. These data support the functional role of FBXO32 as a potential tumour suppressor.

DETAILED DESCRIPTION OF THE INVENTION

The present invention provides a method of inducing apoptosis in a tumour cell and of modulating pluripotency and/or self-renewing characteristics of a stein/progenitor cell. Apoptosis is a programmed cell death and typically a mechanism in a multicellular organism to remove undesired cells. Where a cell's capability to undergo or initiate apoptosis is impaired or abolished, a damaged cell is able to proliferate in an unchecked manner, thereby developing into a cancer cell. An apoptotic cell shows a characteristic morphology, by which it can be identified under a microscope.

The multitude of cells such as cells of the human or animal body is generated through the process of differentiation. This process of a cell involves numerous signaling cascades. Mature cells of the various tissues of an organism arise from progenitor cells, which possess a broad developmental potential and replicative capacity. Peripheral blood for example contains progenitor cells that can differentiate into endothelial or vascular smooth muscle cells. Progenitor cells in turn originate from stem cells, which have also been identified in most tissues. Stem cells are fully undifferentiated cells that are able to differentiate into any mature functional cells, such as heart, liver, brain cells etc., while retaining the ability to proliferate indefinitely.

Some factors that are known to regulate stem-cell and differentiation-specific genes, such as proteins of the Wnt, TGFβ, FGF, Notch and hedgehog signalling pathways, are proteins of the polycomb-repressive complexes, for example of polycomb-repressive complex 1 or polycomb-repressive complex 2 (Bracken, A. P. et al., *Genes Dev.* (2006) 20, 1123-1136).

By inducing apoptosis in a tumour cell, a method according to the present invention may be used as a therapy for the treatment or prevention of cancer. In some embodiments a respective tumour cell may for example be a breast cancer cell. In some embodiments a respective tumour cell may be cultured. As an illustrative example, a tumour cell may be a cell of a human breast carcinoma cell line, such as MCF-7, MB-468, SK-BR-3, and T47D. A tumour cell may also be obtained from a mammal. In other embodiments the tumour cell line may be included in a mammal, such as for example a rat, a cow, a pig, and a human.

While stem cells such as embryonic stem cells can be differentiated in a controlled fashion, for instance into neurons in the presence of nerve growth factor and retinoic acid (Schuldiner et al. (2001) *Br. Res.* 913, 201-205), their ability to readily differentiate has posed a major practical challenge. In order to maintain embryonic stem cells in a pluripotent state, their differentiating during handling and growing in culture has to be prevented. For this reason they are traditionally cultured in the presence of fetal calf serum on a layer of feeder cells (see e.g. U.S. Pat. No. 5,843,780 and U.S. Pat. No. 6,090,622) or in fibroblast-conditioned medium (CM). Nevertheless, even under carefully controlled conditions embryonic stem cells may undergo spontaneous differentiation during in-vitro propagation. Leukaemia inhibitory factor (LIF), a factor mediating self-renewal in mouse embryonic stem cells, has also been found to inhibit differentiation of mouse embryonic stem cells, but it does not replace the role of feeder cells in preventing differentiation of human embryonic stem cells. Therefore, those skilled in the art will appreciate the method for modulating, including maintaining, pluripotency and/or self-renewing characteristics of a stem cell as a significant improvement.

Adult stem cells, although not pluripotent like embryonic stem cells, have been shown to be capable of self-renewal and to be of a plasticity rendering their developmental capabilities comparable to those of the more immature pluripotent embryonic stem cells. As an example, an adult stem cell is able to differentiate into a cell lineage different from its tissue of origin.

The method for modulating pluripotence and/or self-renewing characteristics of the present invention is suitable for any stem cell, progenitor cell, teratoma cell or any cell derived therefrom. Typically, a respective cell is able to express the components of at least one polycomb repressive complex (see also below). As an illustrative example, any pluripotent human embryonic stem cell or a respective cell line may be used in the respective method. Means of deriving a population of such cells are well established in the art (cf. e.g. Thomson, J. A., et al. [1998] *Science* 282, 1145-1147 or Cowan, C. A., et al. [2004] *N. Engl. J. Med.* 350, 1353-1356). Furthermore, 71 independent human embryonic stem cell lines are for example known to exist, of which 11 cell lines are available for research purposes (see e.g. the NIH Human Embryonic Stem Cell Registry at http://stemcells.nih.gov/research/registry/eligibilityCriteria.asp), such as GE01, GE09, BG01, BG02, TE06 or WA09. Adult stem cells may for instance be isolated from blood from the placenta and umbilical cord left over after birth, or from myofibers, to which they are associated as so called "satellite cells" (Collins, C. A., et al. [2005] *Cell* 122, 289-301, see also Rando, T. A., [2005] *Nature Medicine* 11, 8, 829-831).

The term "stem cell" as used herein refers to any stem cell and also includes a so called cancer stem cell. Many types of cancer have been found to include such cancer stem cells, which are characterized by their self-renewing capacity and differentiation ability. A wide range of studies show that most cancers are clonal and may represent the progeny of a single cancer stem cell endowed with the capacity to maintain tumour growth. Krivtsov et al. (*Nature* (2006) 442, 818-822) have for example purified a cell population highly enriched for progenitor-derived leukaemia stem cells and characterised them by gene expression profiling. They report that these cells resemble the progenitor from which they arose, but express a self-renewal-associated programme normally expressed in haematopoietic stem cells (ibid.).

Malignant tumours can be viewed as an abnormal organ in which a single cancer stem cell or a small population thereof have escaped the normal limits of self-renewal, thereby giving rise to abnormally differentiated cancer cells that contribute to tumour progression and growth. Eradication of such cancer stem cells is assumed to be a critical part of any successful anti-cancer therapy, and to explain why conventional cancer therapies are often only effective in reducing tumour burden, but not curative. Modulating pluripotency and/or self-renewing characteristics of a stem/progenitor cell may for example include inducing differentiation of a stem cell, such as a cancer stem cell. This may, for example, be carried out via an inhibition of histone methylation (see also below). By modulating pluripotency and/or self-renewing characteristics of a stem/progenitor cell, a method according to the present invention may accordingly for instance be a therapy for the treatment or prevention of cancer.

Stem cells are also found in carcinomas called teratoma of various tissues (often of the testes and the ovary) that produce tissues consisting of a mixture of two or more embryological layers. The malignant forms of such carcinomas are also called teratocarcinoma. By modulating pluripotency and/or self-renewing characteristics of a stem/progenitor cell, a method according to the present invention may accordingly for instance also be a therapy for the treatment or prevention of teratoma. Modulating pluripotency and/or self-renewing characteristics of a stem/progenitor cell may, for example, include maintaining these pluripotency and/or self-renewing characteristics, and thus also inhibiting differentiation of a stem/progenitor cell, in particular of "healthy" stem cells that may be beneficial for in vivo or in vitro uses.

Where the method is intended to be used for a progenitor cell, i.e. a cell giving rise to mature somatic cells, any progenitor cell may be used in this method of the invention. Examples of suitable progenitor cells include, but are not limited to, neuronal progenitor cells, endothelial progenitor cell, erythroid progenitor cells, cardiac progenitor cells, oligodendrocyte progenitor cells, retinal progenitor cells, or haematopoietic progenitor cells. Methods of obtaining progenitor cells are well known in the art. As two illustrative examples, a method of obtaining megakaryocyte progenitor cells has been disclosed in US patent application 2005/0176142 and a method of obtaining mouse liver progenitor cell lines has been described by Li et al. ((2005) *Stem Cell Express*, doi: 10.1634/stemcells.2005-0108).

A method according to the present invention includes administering to a respective tumour cell or to a respective stem/progenitor cell a compound of the following general formula (I)

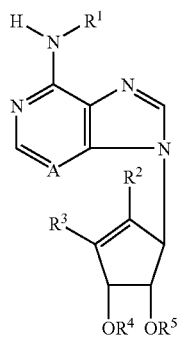

In this general formula (I), A represents C or N. $R^1$, $R^4$ and $R^5$ may be H or independently selected aliphatic, cycloaliphatic, aromatic, arylaliphatic, and arylcycloaliphatic hydrocarbyl groups, which include 0-6, in some embodiments 0-4, and in some embodiments 0-3 heteroatoms selected from the group N, O, P, S, Se and Si. In some embodiments $R^4$ and $R^5$ may be identical. In some embodiments $R^4$ and $R^5$ may be linked so as to define an aliphatic hydrocarbyl bridge. A respective hydrocarbyl bridge may for example include 1-12, in some embodiments 2-10, and in some embodiments 2-8 main chain carbon atoms and contain 1-5, in some embodiments 1-4, and in some embodiments 1-3 heteroatoms selected from the group N, O, P, S, Se, and Si. $R^2$ may be H or a halogen atom, such as F, Cl, Br or I. In some embodiments $R^2$ is F or Cl. $R^3$ may be H, or an aliphatic, cycloaliphatic, aromatic, arylaliphatic or arylcycloaliphatic hydrocarbyl group. This hydrocarbyl group may include 1-12, in some embodiments 1-8, and in some embodiments 1-4, main chain carbon atoms and 0-4, such as 0-3 or 0-2 heteroatoms selected from the group N, O, P, S, Se, Si, and halogen, such as F or Cl.

The term "aliphatic" means, unless otherwise stated, a straight or branched hydrocarbon chain, which may be saturated or mono- or polyunsaturated. An unsaturated aliphatic group contains one or more double and/or triple bonds. The branches of the hydrocarbon chain may include linear chains as well as non-aromatic cyclic elements. The hydrocarbon chain, which may, unless otherwise stated, be of any length, and contain any number of branches. Both the main chain as well as the branches may furthermore contain heteroatoms as for instance N, O, S, Se or Si.

The term "alicyclic" means, unless otherwise stated, a nonaromatic cyclic hydrocarbon moiety, which may be saturated or mono- or polyunsaturated. The cyclic hydrocarbon moiety may be substituted with nonaromatic cyclic as well as chain elements. The main chain of the cyclic hydrocarbon moiety may, unless otherwise stated, be of any length and contain any number of non-aromatic cyclic and chain elements. Both the cyclic hydrocarbon moiety and the cyclic and chain substituents may furthermore contain heteroatoms, as for instance N, O, S, Se or Si.

The term "aromatic" means, unless otherwise stated, a planar cyclic hydrocarbon moiety of conjugated double bonds, which may be a single ring or include multiple fused or covalently linked rings. The main chain of the cyclic hydrocarbon moiety may, unless otherwise stated, be of any length and contain any number of heteroatoms, as for instance N, O and S.

By the term "arylaliphatic" is meant a hydrocarbon moiety, in which one or more aryl groups are attached to or are substituents on one or more aliphatic groups. Thus the term "arylaliphatic" includes for instance hydrocarbon moieties, in which two or more aryl groups are connected via one or more aliphatic chain or chains of any length, for instance a methylene group.

Each of the terms "aliphatic", "alicyclic", "aromatic" and "arylaliphatic" as used herein is meant to include both substituted and unsubstituted forms of the respective moiety. Substituents my be any functional group, as for example, but not limited to, amino, amido, azido, carbonyl, carboxyl, cyano, isocyano, dithiane, halogen, hydroxyl, nitro, organometal, organoboron, seleno, silyl, silano, sulfonyl, thio, thiocyano, trifluoromethyl sulfonyl, p-toluenesulfonyl, bromobenzenesulfonyl, nitrobenzenesulfonyl, and methanesulfonyl.

In some embodiments the present invention relates to the use of a compound of the above formula for inducing apoptosis in a tumour cell and/or modulating pluripotency and/or self-renewing characteristics of a stem/progenitor cell. A respective use may for example be the manufacture of a medicament for this purpose.

Figure 1A:
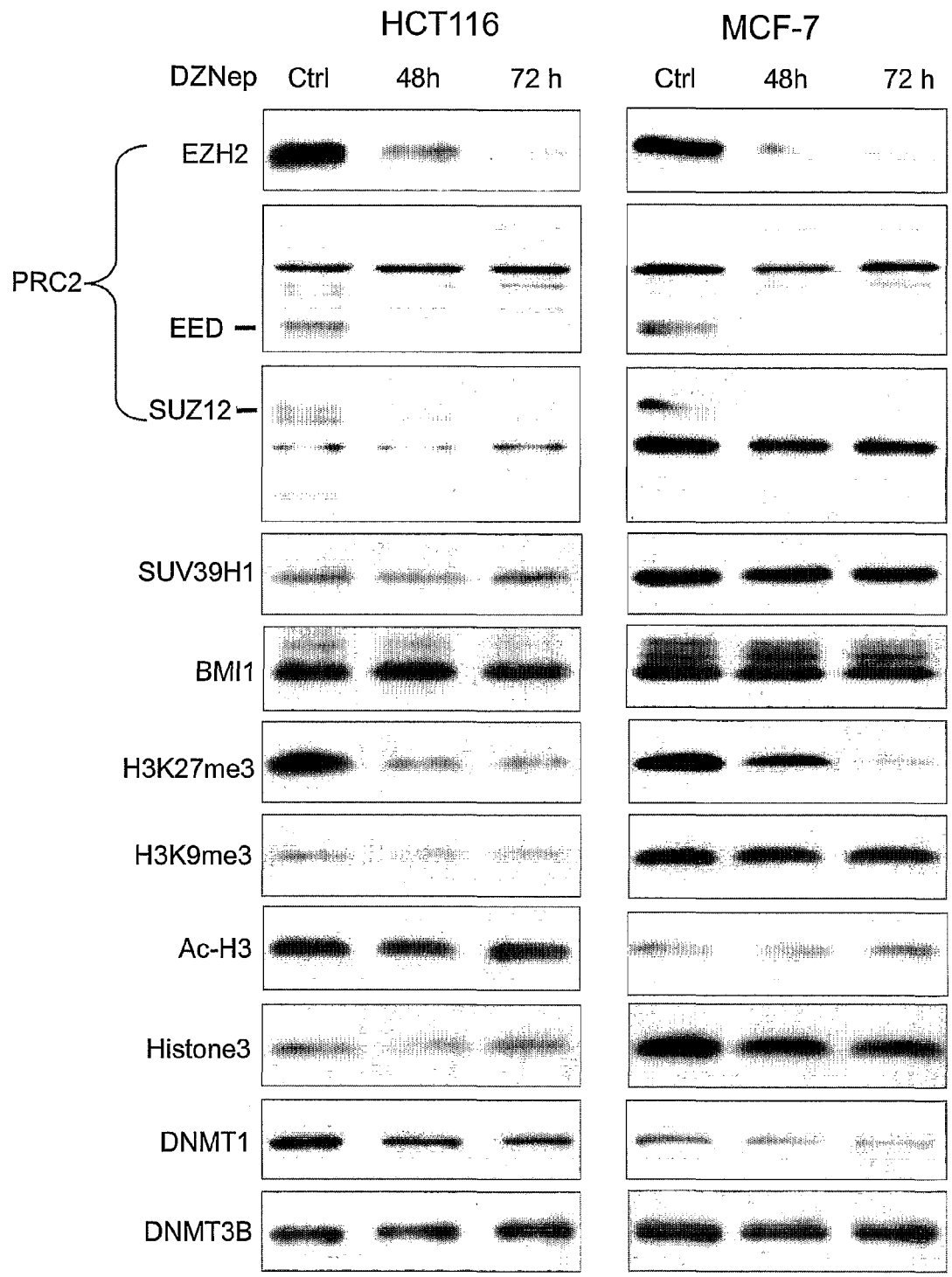
FIG. 1A depicts a Western blot analysis of HCT116 (left) and MCF-7 cells (right) treated with 5 µM 3-deazaneplanocin (DZNep) for 48 and 72 hours, and without DZNep treatment (control). Protein levels of the PRC2 components SUZ12, EZH2 and EED were drastically reduced. No effect on Suv39h1 and Blim 1 expression levels was observed. Levels of DNA methyl-transferases DNMT1 and DNMT3b, which mediate DNA methylation, were not affected. Trimethylation of lysine 27 of histone 3 (H3-K27), was however strongly reduced, while no effect on methylation of lysine 9 of histone H3 (H3-K9) was observed.
Figure 2:
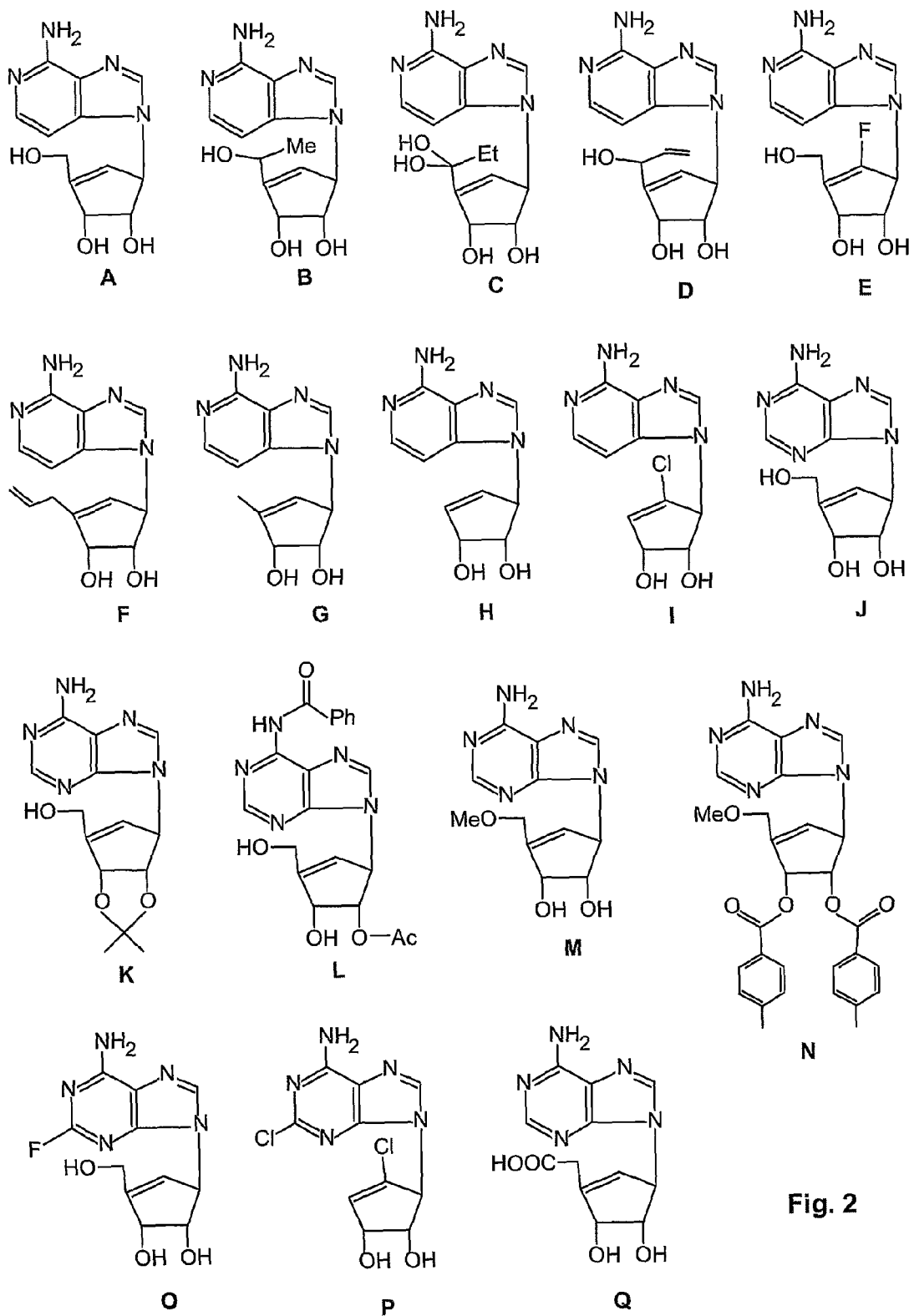
FIG. 2 shows the structure of illustrative examples of compounds that may be used for inducing apoptosis in a tumour cell: A: 3-deazaneplanocin A, 5-(4-amino-1H-imidazo[4,5-c]pyridin-1-yl)-3-(hydroxymethyl)-3-cyclopentene-1,2-diol, Chemical Abstracts No. 102052-95-9; B: 5-(4-amino-1H-imidazo[4,5-c]pyridin-1-yl)-3-(1-hydroxyethyl)-3-cyclopentene-1,2-diol, Chemical Abstracts No. 146424-81-9; C: 5-(4-amino-1H-imidazo[4,5-c]pyridin-1-yl)-3-(1,1-dihydroxypropyl)-3-cyclopentene-1,2-diol, CAS-No. 851071-63-1; D: 5-(4-amino-1H-imidazo[4,5-c]pyridin-1-yl)-3-[1-hydroxy-2-propenyl]-3-cyclopentene-1,2-diol, CAS-No. 851071-61-9; E: 5-(4-amino-1H-imidazo[4,5-c]pyridin-1-yl)-4-fluoro-3-(hydroxymethyl)-3-cyclopentene-1,2-diol, CAS-No. 127828-67-5; F: 5-(4-amino-1H-imidazo[4,5-c]pyridin-1-yl)-3-(2-propenyl)-3-cyclopentene-1,2-diol, CAS-No. 851071-58-4; G: 5-(4-amino-1H-imidazo[4,5-c]pyridin-1-yl)-3-methyl-3-cyclo-pentene-1,2-diol, CAS-No. 224453-13-8; H: 5-(4-amino-1H-imidazo[4,5-c]pyridin-1-yl)-3-cyclopentene-1,2-diol, CAS-No. 111005-71-1; I: 5-(4-amino-1H-imidazo[4,5-c]pyridin-1-yl)-4-chloro-3-cyclopentene-1,2-diol, CAS-No. 127828-64-2; J: 5-(6-amino-9H-purin-9-yl)-3-(hydroxymethyl)-3-cyclopentene-1,2-diol, CAS-No. 88824-06-0; K: 4-(6-amino-9H-purin-9-yl)-3a,6a-dihydro-2,2-dimethyl-4H-cyclopenta-1,3-dioxole-6-methanol, CAS-No. 88824-08-2; L: N-[9-[5-(acetyloxy)-4-hydroxy-3-(hydroxymethyl)-2-cyclopenten-1-yl]-9H-purin-6-yl]-benzamide, CAS-No. 83844-33-1; M: 5-(6-amino-9H-purin-9-yl)-3-(methoxy-methyl)-3-cyclopentene-1,2-diol, CAS-No. 138571-48-9; N: 4-methyl-benzoic acid [3-(6-amino-9H-purin-9-yl)-4-hydroxy-5-[(4-methylbenzoyl)oxy]-1-cyclopenten-1-yl]methyl ester, CAS-No. 142888-07-
Figure 2:
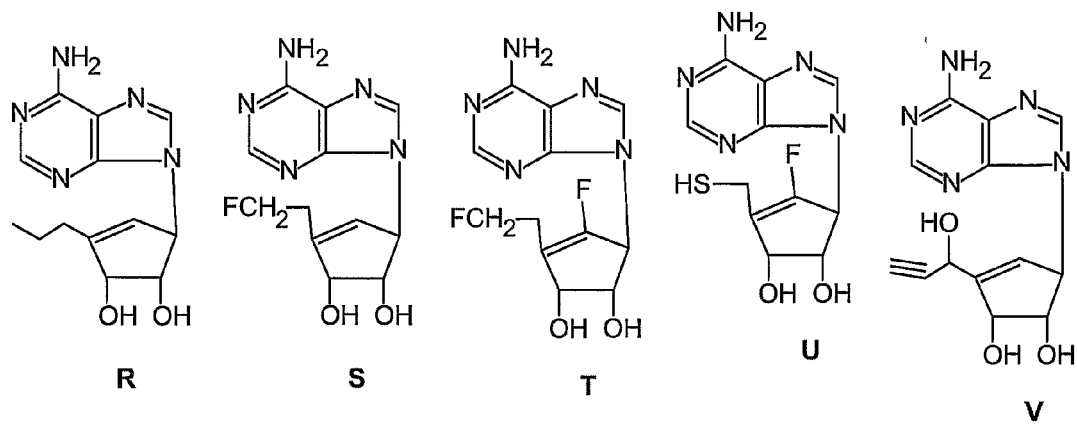

A number of suitable compounds are illustrated in FIG. 2. The depicted compounds can be addressed as analogues (partly carbocyclic analogues) of adenosine. As an example, in one embodiment the compound is 3-deazaneplanocin (see FIG. 2A). As a further example, in another embodiment the compound is Neplanocin A (see FIG. 1K).

These compounds are so far known for their broad-spectrum antiviral effect, such as inhibition of the Herpes Simplex Type I virus or the Ebola virus (Tseng, C. K. H., et al., *J. Med. Chem.* (1989), 32, 1442-1446; Glazer, R. I., et al., *Biochem. Biophys. Res. Commun.* (1986), 135, 2, 688-694; De ClercQ, E., et al., *Antimicrobial Agents and Chemotherapy* (1989), 33, 8, 1291-1297; U.S. Pat. No. 4,968,690; European patent application 0 510 260). This effect has been attributed to an inhibition of the enzyme S-adenosylhomocysteine synthase, as well as an augmentation of interferon production in the host (Glaser et al., 1986, supra; Bray, M, et al., *Antiviral Research* (2002), 55, 1, 151-159). It has previously been reported that respective compounds are not toxic to normal host cells in antivirally effective concentrations (De ClercQ, E., *Clinical Microbiology Reviews* (2001), 14, 2, 382-397).

Accordingly, the method of the invention includes the use of a compound as defined above, including the use in the manufacture of a medicament. In one aspect the present invention also relates to the use of a compound as defined above for inducing apoptosis in a tumour cell and/or modulating pluripotency and/or self-renewing characteristics of a stem/progenitor cell. In this regard the present invention also relates to a compound as defined above for inducing apoptosis in a tumour cell and/or modulating pluripotency and/or self-renewing characteristics of a stem/progenitor cell. It is understood that the forgoing and following explanations likewise apply to a respective use and to a compound for the said application(s).

In some embodiments a method according to the present invention is an epigenetic therapy. The respective method may for example include an inhibition of histone methylation—a central epigenetic modification in eukaryotic chromatin, such as the methylation of lysine 27 on histone 3. As an illustrative example, a method according to the present invention may include depleting in the respective tumour cell, stem cell or progenitor cell a polycomb repressive complex. Polycomb repressive complex (PRC) proteins are known to divide into two major separate complexes (see e.g. Cao and Zhang, 2004). The first complex, which includes homologues of the *Drosophila esc* and E(z) genes, has histone deacetylase activity. The second PcG complex (dPRC-1 in *Drosophila*, mPRC1 in mice and hPRC-H in humans) contains homologues of the *Drosophila* Pc, Psc, Ph, RING and Scm genes and can mediate silencing of target genes by interfering with the SWI/Snf ("switch/sucrose nonfermenting") chromatin remodelling machinery, blocking transcriptional initiation and the recruitment of additional silencing activities.

The method of the present invention may for example include depleting a polycomb repressive complex that can be classified as falling under the first complex as described above. Examples of such a complex include polycomb repressive complex 2, polycomb repressive complex 3, and polycomb repressive complex 4. As an illustrative example, components of polycomb repressive complex 2 include for instance EZH2, SUZ12, EED and RbAp48. As a further illustrative example, components of polycomb repressive complex 3 include EZH2, SUZ12, RbAp46/48, and two lower molecular weight isoforms of EED (Kuzmichev, A., et al., *Molecular Cell* (2004), 14, 2, 183-193). As yet a further illustrative example, components of polycomb repressive complex 4 include inter alia EZH2 and SIRT1 (Kuzmichev, A., et al., *Proc. Natl. Acad. Sci. U.S.A*. (2005), 102, 6, 1859-1864).

Any component of a selected polycomb repressive complex may be depleted in the present method of the invention. Those skilled in the art will be aware of the fact that the protein levels of components of a polycomb repressive complex in part depend on the presence of other components of the complex (see FIG. 3E, see also e.g. Pasini, D., et al., *EMBO Journal* (2004), 23, 4061-4071). Depleting one component of a polycomb repressive complex thus typically also decreases the levels of other components of the respective polycomb repressive complex. As an illustrative example, the level of SUZ12, EZH2 or EED may be depleted.

Both of the above described major polycomb-repressive complexes have been found to co-occupy the promoter regions of a large set of genes in embryonic stem cells (Boyer, L. A., et al., *Nature* (2006) 441, 349-353), most of the target genes being transcription factors with important roles in a variety of developmental processes. A large number of these transcription factors possess essential roles in development, such as homeodomain-containing factors, which determine cell fate during embryonic development.

The Polycomb group genes are furthermore known as a set of regulatory proteins involved in maintenance, including silencing, of expression patterns controlling development. Polycomb group (PcG) complexes are responsible for long-term silencing of genes by altering chromatin structure and thereby altering the accessibility of DNA to factors required for gene transcription (for an overview see Sparmann, A., & van Lohuizen, M., *Nature Reviews Cancer* (2006) 6, 846-856). Polycomb group (PcG) complexes act through epigenetic modification, such as deacetylation of histone tails, and by inhibiting ATP-dependent chromatin remodeling (Levine, S. S., et al., *Trends Biochem Sci* (2004) 29, 478-85; Lund, A. H., and van Lohuizen, M., *Curr Opin Cell Biol* (2004) 16, 239-46). As an example, the polycomb repressive complex 2 (PRC2) is a protein complex known to be involved in the initiation of epigenetic silencing. PRC2 is often overexpressed in human cancer and thus considered to be a promising target for cancer epigenetic therapy. The Polycomb group proteins are highly conserved from *Drosophila* to human, and form multiple Polycomb Repressive Complexes. The components of polycomb repressive complexes contain intrinsic histone methyltransferase (HMTase) activity and maintain gene silencing through methylation of core histones (Muller, J., et al. *Cell* (2002) 111, 197-208; Cao, R. et al. *Science* (2002) 298, 1039-1043; Milne, T. A., et al. *Mol Cell* (2002) 10, 1107-17; Nakamura, T., et al., *Mol Cell* (2002) 10, 1119-1128; Beisel, C., et al. *Nature* (2002) 419, 857-62).

Among PcG proteins, polycomb repressive complex 2 has previously been linked to stem cell self-renewal and cancer (Lee, T. I. et al., *Cell* (2006) 125, 301-313; Holden, C. *Science* (2006) 312, 349; Kamminga, L. M. et al. *Blood* (2006) 107, 2170-2179). In human mammary epithelial cells with lost activity of $p16^{INK4A}$ (an early event in tumourigenesis) an up-regulation of two components of polycomb repressive complex 2 has for example been observed (Reynolds, P A et al., *J Biol Chem* (2006) 281, 34, 24790-24802). Polycomb repressive complex 2 contains three core components: EZH2 (human enhancer of Zeste homolog), SUZ12 (suppressor of zeste 12 homolog), and EED (embryonic ectoderm development; see e.g. Levine et al., 2004, supra). EZH2 is the active component of PRC2 with histone methyltransferase activity (e.g. Viré, E., et al., *Nature* (2006), 439, 16, 871-874), and SUZ12 and EED are required for this activity in both somatic cells and stem cells (Schoeftner, S., et al., *EMBO Journal* (2006) 25, 3110-3122). EZH2 catalyses histone H3 lysine-27 (H3-K27) methylation, and this enzymatic activity is required for PRC2-mediated gene silencing (Muller, J. et al. *Cell* (2002), 111, 197-208; Cao, R. et al., *Science* (2002), 298, 1039-43; Milne, T. A. et al., *Molecular Cell* (2002), 10, 1107-17, Beisel, C., et al., *Nature* (2002), 419, 857-62; Chen, H., et al., *J. Biol. Chem* (2005), 280, 23, 22437-22444). Polycomb repressive complex 1, which has been suggested to maintain gene silencing, is able to recognize lysine-27 methylated histone H3.

In *Drosophila*, polycomb group proteins are recruited to target sites through interaction with site-specific DNA-binding proteins. The exact mechanism of recruitment to target genes in mammals is currently not known. It is however known that histone methylation alters the properties of the nucleosome (the basic repeating unit of chromatin), affecting its interactions with other proteins. As a result transcription is repressed. Furthermore histone methylation is thought to function in concert with DNA methylation in chromatin silencing, a further mechanism associated with epigenetic silencing.

There have been indications for direct links between histone methylation and DNA methylation. As an example, methylated lysine-27 of histone H3 serves as an anchorage point for the recruitment of further proteins. Furthermore, EZH2 binds to DNA methyltransferases and to bind to the promoter of its target genes together with these enzymes (Viré, et al, 2006, supra), thus causing methylation of promoters of target genes and subsequent silencing of these genes. Accordingly, an upregulation of EZH2 and SUZ12 has been found to coincide with an enrichment of DNA methyltransferases, with DNA methylation of a number of loci, and a methylation of lysine-27 of histone H3 (Reynolds et al., 2006, supra). Following depletion of EZH2, but not while EZH2 and DNA methyltransferases were bound to the promoter, binding of RNA polymerase to the promoter occurred (Viré, et al, 2006, supra).

The human EZH2, and its associated H3-lysine-27 methyltransferase activity, has been linked to cancer and was found to be overexpressed in late-stage prostate cancer and breast cancer (Saramaki, O. R. et al., *Genes, Chromosomes & Cancer* (2006) 45, 639-645), expression and protein levels of EZH2 were for example found higher in metastatic hormone-refractory prostate cancer than in primary untreated tumours. In addition to EZH2, SUZ12, another component of PRC2 complex, was also found to be upregulated in several human tumours, including colon, breast, and liver tumours (Kirmizis, A., et al., *Molecular Cancer Therapeutics* (2003) 2, 113-121; Kirmizis, A., et al., *Genes & Development* (2004) 18, 1592-1605).

While DNA methylation as such is essential for the survival of somatic cells, it does not play an essential role in maintaining embryonic stem cells in an undifferentiated state. Nevertheless the genes occupied by PRC1 and PRC2 in embryonic stem cells are likewise reported to be enriched in methylated histone H3 lysine-27 (Boyer et al., 2006, supra). Furthermore, the methylated lysine of this histone was also associated with probes close to the transcription start site of the respective genes. The data of Boyer et al. suggest that in embryonic stem cells the binding of polycomb group proteins directly silences genes, and that the activation of these genes correlates with differentiation and loss of pluripotency.

The polycomb repressive complex 2 component EED is furthermore known to contribute to silencing in undifferentiated cells by its enrichment on the inactive X-chromosome in female mammals in cells of the early mouse embryo and trophoblast stem and progenitor cells. In the absence of EED differentiation induces reactivation of the paternal X-chromosome (Kalantry, S., et al., *Nature Cell Biol*. (2006), 8, 2, 195-202). EED has also been found to be required for the formation of the PRC2 complex on the inactive X-chromosome and for the methylation of lysine-27 of histone H3 in undifferentiated and trophoblast stern cells (ibid. and Schoeftner et al., 2006, supra). With regard to the two proteins Ezh2 and Suz12, loss of these proteins has been found to lead to a marked loss of cell proliferation in the inner cell mass and early embryonic lethality.

The transcription factors Oct4 and Nanog, which have been identified as being important for the general control of the differentiation status of a cell and for the normal development of pluripotent cells and/or in modulating the pluripotent cell state (e.g. Nichols, J. et al. (1998) *Cell* 95, 379-391; and Mitsui et al (2003) *Cell* 113, 631-642), are known to be associated with low levels of methylation of lysin-27 of histone 3 in embryonic stern cells (Boyer et al., 2006, supra). The PRC2 complex protein SUZ12 has furthermore been shown to regulate a number of genes that are also regulated by Oct4 (Squazzo, S. L., et al., *Genome Research* (2006) 16, 890-900). Knockdown of Oct4 by siRNA furthermore lead to a loss of SUZ12 from a number of target promoters (ibid.). Additionally, in human embryonic cells a significant correlation between genes associated with pluripotency factors Oct4, Sox2, and Nanog, and identified PcG target genes has been reported (Boyer et al., 2006, supra, supplement). 45 target genes were found to be co-occupied by Oct4, Sox2, Nanog and PcG proteins (ibid). These findings illustrate the integration of prc2 proteins into the regulation of cell differentiation and the maintenance of the pluripotent state of stem cells.

Depleting a component of polycomb repressive complex 2, polycomb repressive complex 3, or polycomb repressive complex 4 according to a method of the present invention further results in demethylation of lysine 27 of histone 3 (H3-K27; cf. FIG. 1A). These polycomb repressive complexes are known to trimethylate Lysine 27 of histone H3 in vivo, and Lysine 26 of histone H1 in vitro. In some embodiments of a method according to the invention, the methylation status of lysine 27 of histone 3 may therefore be determined. This may for example be desired to confirm depletion of a polycomb repressive complex.

Where desired, a control measurement may include depleting a component of a polycomb repressive complex by other known means, for instance by means of a nucleic acid molecule. A respective nucleic acid molecule may for instance be a non-coding nucleic acid molecule, such as for example an aptamer or a Spiegelmer® (described in WO 01/92655). A non-coding nucleic acid molecule may also be an nc-RNA molecule (see e.g. Costa, F F, *Gene* [2005], 357, 83-94 for an introduction on natural nc-RNA molecules). Examples of nc-RNA molecules include, but are not limited to, an antisense-RNA molecule, an L-RNA Spiegelmer®, a silencer-RNA molecule (such as the double-stranded Neuron Restrictive Silencer Element), a micro RNA (miRNA) molecule, a short hairpin RNA (shRNA) molecule, a small interfering RNA (si-RNA) molecule or a repeat-associated small interfering RNA (rasiRNA) molecule.

The use of small interfering RNAs, short hairpin and micro RNAs has become a tool to "knock down" specific genes. It makes use of gene silencing or gene suppression through RNA interference (RNAi), which occurs at the posttranscriptional level and involves mRNA degradation. RNA interference represents a cellular mechanism that protects the genome. SiRNA and miRNA molecules mediate the degradation of their complementary RNA by association of the siRNA with a multiple enzyme complex to form what is called the RNA-induced silencing Complex (RISC). The siRNA or miRNA becomes part of RISC and is targeted to the complementary RNA species which is then cleaved. siRNAs are perfectly base paired to the corresponding complementary strand, while miRNA duplexes are imperfectly paired. Activation of RISC leads to the loss of expression of the respective gene (for a brief overview see Zamore, P D, Haley, B *Science* [2005], 309, 1519-1524). It has been observed that the strongest silencing occurs with sequences that do not form secondary structures (Patzel, V., et al. *Nature Biotech*. [2005] 23, 1440-1444). Persons skilled in the art thus typically avoid using sequences that for instance are known to form a loop. This can be done by exchanging selected bases to a base that is still able to form a wobble pairing with the target sequence (Patzel, V et al., supra). The siRNA/miRNA technique has for example been applied to silencing parasitic DNA sequences, such as the cleavage of HIV RNA, as disclosed in US patent application 2005/0191618.

A respective siRNA/shRNA/miRNA molecule may be directly synthesized or expressed within a cell of interest (including a cell that is part of a microorganism and an animal), for example by means of a vector under the control of an inducible or constitutive promoter. It may also be introduced into a respective cell and/or delivered thereto. One illustrative example of delivering a siRNA, shRNA or miRNA molecule into selected cells in vivo is its non-covalent binding to a fusion protein of a heavy-chain antibody fragment ($F_{ab}$) and the nucleic acid binding protein protamin (Song, E. et al., *Nature Biotech*. (2005), 23, 6, 709-717). Another illustrative example of delivering a siRNA molecule into selected cells in vivo is its encapsulation into a liposome. Morrissey et al. *Nature Biotech*. (2005), 23, 8, 1002-1007) for instance used a stable nucleic acid-lipid-particle, coated with a polyethylene glycol-lipid conjugate, to form liposomes for intravenous administration. Where it is desired to apply nanoparticles for delivering siRNA or miRNA, a suitable approach of their cell-specific targeting has been described by Weissleder et al. (*Nature Biotech*. (2005), 23, 11, 1418-1423). Yet a further example of delivering a siRNA, shRNA or miRNA molecule to a selected target cell is the use of a biological vehicle such as a bacterium or a virus that includes the respective nucleic acid molecule. Xiang et al (*Nature Biotech*. (2006), 24, 6, 697-702) have for instance used this approach by administering the bacterium *E. coli*, which transcribed from a plasmid inter alia both shRNA and invasin, thus permitting entry into mammalian cells and subsequent gene silencing therein.

An illustrative example of siRNA molecules is depicted in FIG. 3I and FIG. 3J.

In some embodiments of a method according to the present invention depleting the polycomb repressive complex causes the release of a complex between said polycomb repressive complex and a tumour suppressor gene. In some of these embodiments a tumour suppressor gene is reactivated thereby causing apoptosis in the respective cell. The present inventors have found that FBX032 is an example of a respective tumour gene (see e.g. FIGS. 6B and 6D-6H). FBX032 encodes an ubiquitin ligase (of the same name) that is known to target specific proteins for proteolysis at the proteasome. FBX032 has so far been considered an important gene for muscle development. Examples of FBX032 include, but are not limited to, the human protein of 355 amino acids with the UniProtKB/Swiss-Prot accession number Q969P5, the mouse protein of 355 amino acids with the UniProtKB/Swiss-Prot accession number Q9CPU7, or the rat protein of 350 amino acids with UniProtKB/Swiss-Prot accession number Q91Z62. An illustrative example of a respective gene is the human gene that transcribes mRNA of the sequence of EMBL nucleotide sequence database accession number BC024030, as well as EMBL accession numbers BC120963 and BC120964. As a further example, the porcine FBX032 gene has also been mapped and sequenced (Yu, J., et al. *Animal Genetics* (2005) 36, 5, 451-452).

Those skilled in the art will appreciate that the present method of the invention preferentially induces apoptosis in cancer cells (see e.g. FIG. 3a). A time-dependent cell death response is typically observed in a tumour cell. A respective tumour cell may for instance be cultured. It may for instance be a cell of a cell line, such as MCF-7, MB-468, SK-Br-3, T47D, HCT116, RKO or SW480. In some embodiments a respective tumour cell may be obtained from a mammal. In other embodiments a respective tumour cell may be included in a mammal. The tumour cell may be of any type of tumour, such as for instance a breast cancer cell.

Where desired, the progress of apoptosis in a tumour cell may be monitored, for example by propodium iodide staining or flow cytometry analysis (see FIG. 3A), mitochondrial dysfunction (JC-1 staining) or caspase 3 activation (see e.g. FIGS. 3B and 3D). As can be inferred from these illustrations, the method of the invention generally triggers an apoptotic cell death response involving mitochondria disruption and caspase activation. These illustrations also show that non-cancerous cells, such as MCF10A cells and normal primary colon epithelial CC33D cells show only a marginal cell death response, if any at all (cf. also FIG. 3D). Besides determining apoptosis in a respective cell in some embodiments a method according to the present invention may include determining cell viability in a respective cell. Respective methods are well established in the art.

In some embodiments a method according to the present invention includes contacting a respective cell with a predetermined quantity of a compound of the general formula (I) (see above), such as a tumour cell, stem cell or progenitor cell. In some embodiments at least two different predetermined quantities of a compound of the general formula (I) are used. In some of these embodiments at least a first and a second tumour cell are used. The first tumour cell is contacted with the lower of the two predetermined quantities and the second tumour cell is contacted with the higher of the two predetermined quantities. Respective embodiments may for example be a screening assay, a cytotoxity test or the determination of a dose/response curve.

In some embodiments the first tumour cell and the second tumour cell are obtained from the same patient. Such a method may for instance be a method of predicting a patient's or an animal's individual response to a compound of the general formula (I). Single nucleotide polymorphisms and individual differences in gene expression usually cause individual differences between patients in responding to a compound that is administered. As an example, single nucleotide polymorphisms of the FBX032 gene have been detected (Yu et al., 2005, supra). In some embodiments a respective method of the invention may also be a method of identifying genetic variants that influence a patient's response to a compound of formula (I). Typically the effect of a compound applied to an animal or a patient as a drug is determined by many proteins, so that composite genetic polymorphisms in multiple genes coupled with nongenetic factors determine a response to a compound. A respective method of the invention may thus be a method of determining a patient's genotype, for example to ensure maximum efficacy with minimal adverse effects.

As indicated above, one method of the present invention is a method for modulating gene expression in a cell. The method includes administering to a respective cell a compound of the general formula (I) (see above). Any cell may be used in the present method of the invention. As an illustrative example, a stem/progenitor cell, including an embryonic stem cell, or a primordial germ cell may be used. It may be desired to use a non-cancer cell, in order to avoid that the present method of the invention shows an apoptotic effect due to its action on endogenous cellular components. Due to the selective action of a compound of formula (I) on cancer cells but not on normal tissue (see below and e.g. FIG. 3F), the present method is on the other hand particularly well suited for normal cells.

Any cell may be used that expresses the components of a polycomb repressive complex. In some embodiments the cell includes an endogenous polycomb repressive complex that is functionally active. In some of these embodiments the respective cell is a stem or a progenitor cell. Examples of stem cells that may be used in the method of the present invention include, but are not limited to, embryonic stem cells, trophoblast stem cells and extraembryonic stem cells. In some embodiments of the methods of the invention an embryonic stem cell, such as an embryonic stem cell of human origin, i.e. a human embryonic stem cell may thus be used. In other embodiments the cell is a progenitor cell (cf., above). In yet other embodiments the cell is a cancer cell (see above). In other embodiments the endogenous polycomb repressive complex is functionally inactive. In some of these embodiments any cell of an established eukaryotic cell line is selected, such as for instance HEIS, COS, CHO, CRE, MT4, DE (duck embryo), QF (quail fibrosarcoma), NSO, BHK, Sf9, PC12, or High 5. In yet further embodiments one or more exogenous genes encoding components of the respective polycomb repressive complex are introduced by means of recombinant technology, for instance by means of a vector carrying the respective gene.

The selected cell furthermore includes a target gene for the respective polycomb repressive complex, or at least a promoter thereof. An illustrative example of a respective target gene is the FBX032 gene. In some embodiments the selected target gene, or a functional fragment thereof, are endogenously expressed in amounts that are sufficient for the performance of the present method of the invention. In other embodiments the selected transcription factors are largely or entirely absent from the proteome of the cell. In either case the respective target gene, or a functional fragment thereof, may be introduced into the cell by means of one or more recombinant vectors that include the genes encoding the desired target gene. Typically, but not necessarily, the respective genes will be under the control of an active promoter or of a promoter that can be conveniently activated by external stimuli.

Where it is desired to include further copies of the promoter of a respective target gene or the complete target gene, i.e. in addition to the endogenous gene of the respective cell, into a cell of interest, this may likewise be achieved by means of a recombinant vector (e.g. Kawataba, K et al., supra). It may also be advantageous to introduce a vector that contains the respective promoter into the cell for the purpose of facilitating the activation of the promoter (whether of endogenous or exogenous origin). In addition, it may be desired to employ the promoter of a target gene to express an exogenous gene, for instance to obtain a protein. In this case typically a vector will be chosen that includes the desired exogenous gene under the control of the promoter of a target gene. For this purpose the sequence of any desired gene may be included into a respective vector. Persons skilled in the art will be aware that it may be required to co-express additional enzymes in a case where it is desired that a respectively transcribed protein also undergoes posttranslational modifications within the cell used in the method of the present invention.

Examples of exogenous genes that may be used in the present method as being under the control of the promoter of a target gene include, but are not limited to, a reporter gene, a drug resistance gene, an apoptosis gene (so-called "death" gene) or any other gene with desirable expression in a respective cell. In some embodiments a respective gene may also encode a protein of interest. In such a case the method of the invention may be used to express and obtain the respective protein. Where the gene under the control of the promoter of a target gene is an apoptosis gene, the present method may for example be used to eliminate pluripotent cells from a tissue.

A compound as described herein, or a pharmaceutically acceptable salt thereof, can be used per se, or in a pharmaceutical composition where it may be mixed with other active ingredients, as in combination therapy, or a suitable carrier or diluent. In this regard the present invention also relates to a pharmaceutical composition for inducing apoptosis in a tumour cell and/or modulating pluripotency and/or self-renewing characteristics of a stem/progenitor cell.

A respective pharmaceutical composition may for example include a cytotoxic agent such as Taxol®, a tyrosine kinase inhibitor such as Gefitinib (Iressa®) or Gleevec®, a (recombinant) growth factor such as interleukin-11 or interferon-α-2b and interleukin-2, a thymidylate synthase inhinitor, such as Raltitrexed®, or a monoclonal antibody such as Rituximab (MabThera®) or Cetuximab (Erbitux®). A compound as described above may for instance be applied in combination with a compound used in epigenetic therapy (see e.g. Peedicayil, J., *Indian J Med Res* (2006) 123, 17-24 for an overview), and a respective pharmaceutical composition may include such a compound. As an illustrative example, a pharmaceutical composition according to the present invention may include a DNA methyltransferase inhibitor, a DNA demethylating agent, and/or a histone-deacetylase inhibitor.

Examples of a DNA methyltransferase inhibitor include, but are not limited to, 5-azacytidine, decitabine (5-aza-2'-deoxycytidine), 5-fluoro-2'-deoxycytidine, 5,6-dihydro-5-azacytidine, and zebularine (1-(β-d-ribofuranosyl)-1,2-dihydropyrimidin-2-one). Examples of a DNA demethylating agent include, but are not limited to, hydralazine, procainamide, procaine, (−)-epigallocatechin-3-gallate (EGCG), psammaplin A, the oligodeoxynucleotide MB98, and 2-(1,3-Dioxo-1,3-dihydro-2H-isoindol-2-yl)-3-(1H-indol-3-yl)propionic acid (MG98). Examples of a histone-deacetylase inhibitor include, but are not limited to, butyrate, phenylbutyrate, valproic acid, m-carboxycinnamic acid bishydroxamic acid (CBHA), oxamflatin, PDX-101, MS-275, depsipeptide, pyroxamide, scriptaid, suberoylanilide hydroxyamic acid (SAHA), trichostatin (TSA), NVP-LAQ824, LBH589, apicidin, CHAP, trapoxin, N-acetyldinaline, and MS-275.

Pharmaceutical compositions comprising the compounds of the present invention may be manufactured in a manner that is itself known, e.g., by means of conventional mixing, dissolving, granulating, dragée-making, levigating, emulsifying, encapsulating, entrapping or lyophilising processes.

Pharmaceutical compositions for use in accordance with the present invention thus may be formulated in conventional manner using one or more physiologically acceptable carriers comprising excipients and auxiliaries that facilitate processing of the active compounds into preparations that can be used pharmaceutically. Proper formulation is dependent upon the selected route of administration.

Exemplary routes of administration of a respective compound or pharmaceutical composition include oral, transdermal, and parenteral delivery. Suitable routes of administration may, for example, include depot, oral, rectal, transmucosal, or intestinal administration; parenteral delivery, including intramuscular, subcutaneous, intravenous, intramedullary injections, as well as intrathecal, direct intraventricular, intraperitoneal, intranasal, or intraocular injections. One may also administer the compound or pharmaceutical composition in a local rather than systemic manner, for example, via injection of the compound directly into a solid tumour, such as in a depot or sustained release formulation. Furthermore, a respective compound or pharmaceutical composition may be used in a targeted drug delivery system, for example, in a liposome coated with a tumour-specific antibody. Such liposomes may for example be targeted to and taken up selectively by a tumour.

As an illustrative example, for injection, a compound or pharmaceutical composition according to the present invention may be formulated in aqueous solutions, preferably in physiologically compatible buffers such as Hanks's solution, Ringer's solution, or physiological saline buffer. For transmucosal administration, penetrants appropriate to the barrier to be permeated are typically used in the formulation. Such penetrants are generally known in the art.

For oral administration, a respective compound or pharmaceutical composition can be formulated readily by combining the active compound with pharmaceutically acceptable carriers well known in the art. Such carriers enable the compounds of the invention to be formulated as tablets, pills, dragées, capsules, liquids, gels, syrups, slurries, suspensions and the like, for oral ingestion by a patient to be treated.

Pharmaceutical preparations for oral use can be obtained by adding a solid excipient, optionally grinding a resulting mixture, and processing the mixture of granules, after adding suitable auxiliaries, if desired, to obtain tablets or dragée cores. Suitable excipients are, in particular, fillers such as sugars, including lactose, sucrose, mannitol, or sorbitol; cellulose preparations such as, for example, maize starch, wheat starch, rice starch, potato starch, gelatine, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Pharmaceutical compositions that can be used orally include, but are not limited to, push-fit capsules made of gelatine, as well as soft, sealed capsules made of gelatin and a plasticizer, such as glycerol or sorbitol. The push-fit capsules may contain the active compound(s) in admixture with filler such as lactose, binders such as starches, and/or lubricants such as talc or magnesium stearate and, optionally, stabilizers. In soft capsules, the compound(s) may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, a respective pharmaceutical composition may take the form of tablets or lozenges formulated in conventional manner.

For administration by inhalation, a pharmaceutical composition for use according to the present invention may conveniently be delivered in the form of an aerosol spray presentation from pressurized packs or a nebuliser, with the use of a suitable propellant, e.g., dichlorodifluoromethane, trichlorofluoromethane, dichlorotetrafluoro-ethane, carbon dioxide or other suitable gas. In the case of a pressurized aerosol the dosage unit may be determined by providing a valve to deliver a metered amount. Capsules and cartridges of e. g. gelatine for use in an inhaler or insufflator may be formulated containing a powder mix of the compound and a suitable powder base such as lactose or starch.

A respective pharmaceutical composition may be formulated for parenteral administration by injection, e.g., by bolus injection or continuous infusion. Formulations for injection may be presented in unit dosage form, e. g., in ampules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions.

In some embodiments an active ingredient, such as a compound as described above, may be in powder form for constitution with a suitable vehicle, e.g., sterile pyrogen-free water, before use.

A respective pharmaceutical composition may also be formulated as a rectal composition such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

In order that the invention may be readily understood and put into practical effect, particular embodiments will now be described by way of the following non-limiting examples.

Examples

Cells and Drug Treatment

Cell lines used in these examples were purchased from the American Type Culture Collection (Manassas, Va.). Cells were maintained in DMEM supplemented with 10% fetal bovine serum with glutamine, penicillin, and streptomycin. For drug treatment, cells were seeded the day before the drug treatment. Cells were treated with 5 μM 3-Deazaneplanocin A or 2 μM 5-aza-2'-deoxycytidine (5-AzaC; Sigma) for 72 hours and trichostatin A (TSA; Sigma) at 100 nM for 24 hours. For co-treatment of cells with 5-AzaC and TSA, 5-Aza was added for 48 hours and followed by TSA for 24 hours.

siRNA

Specific siRNA oligonucleotides targeting EZH2, SUZ12 and EED mRNAs were described previously (Cao, R., & Zhang, Y., *Mol Cell* (2004) 15, 57-67; Bracken, A. P., et al, *EMBO J.* (2006) 22, 5323-35). Bracken et al. used two oligonucleotides in generating the stem-loop RNA that target SUZ12, which were 5'-GATCCCCGTCGCAACGGAC-CAGTTAATTCAAGAGATTAACTGGTCCGTTGCGA CTTTTTGGAAA-3' (SEQ ID NO: 1) and 5'-TCGATTTC-CAAAAAGTCGCAACG GACCAGTTGATCTCTTGAAT-TAACTGGTCCGTTGCGACGGG-3' (SEQ ID NO: 2). Cao & Zhang used for EZH2 the oligonucleotide 5'-AAGACTCT-GAATGCAGTTGCT-3' (SEQ ID NO: 3), and for EED the oligonucleotide 5'-AAGCACTATGTTGGCCATGGA-3' (SEQ ID NO: 4). The Smartpool siRNA duplexes of selected PRC2 targets and the non-targeting control were purchased from Dharmacon (Lafayett, Colo.). FBXO32 siRNA from Sigma-Proligo targets the following sequence: 5'-GTCA-CATCCTTTCCTGGAA-3' (SEQ ID NO: 5). Cells were transfected with 50 nM final concentration of siRNA duplexes using Lipofectamine 2000 (Invitrogen) following the manufacturer's instructions.

Western Blot Analysis

Cell pellets were first lysed in RadioImmuno Precipitation Assay (RIPA) buffer, consisting of an aqueous solution of 25 mM Tris-HCl pH 7.6, 150 mM NaCl, 1% Nonidet-P 40 (NP-40), 1% sodium deoxycholate and 0.1% sodium dodecylsulfate (SDS), before further sonicated using a tissue homogeniser to release all the proteins. Equal amounts of protein were separated on SDS-polyacrylamide gels and transferred to polyvinylidene difluoride (PVDF) membranes. The blots were probed with antibodies against: EED (07-368), SUZ12 (07-379), SUV39H1 (07-550), BMI1 (05-637), tri-methylated H3-K27 (07-449), tri-methylated H3-K9 (07-442) and Acetyl-Histone H3 (06-599), and were purchased from Upstate. EZH2 (AC22) and Histone H3 (3H1) were from Cell Signaling. Antibodies against DNA methyl-transferases DNMT1 and DNMT3B were purchased from Alexis Biochemicals.

Flow Cytometric Analysis

Cells were trypsinised and washed with PBS and fixed in 70% ethanol and processed for propidium iodide staining and FACS analysis. For the caspase 3 activity assay and mitochondrial membrane potential detection, cells were stained with anti-active caspase 3 and JC-1, respectively, according to the manufacturer's instructions (BD Bioscience).

Microarray Analysis and Quantitative Real-Time PCR

Total RNA was isolated from cell lines using Trizol (Invitrogen) and was converted to cDNA using an RNA Amplification kit (Ambion). The microarray hybridisation was performed using the Illumina Gene Expression BeadChip (Illumina) and data analysis was performed using GeneSpring software from Agilent Technologies. Gene expression of normal and primary breast tumor samples was performed using Affymetrix U133A GeneChips (Affymetrix, Santa Clara, Calif.) following the manufacturer's instructions. Gene expression data from individual arrays were normalized by median centering and average linkage hierarchical clustering was done using Cluster and Treeview softwares (http://rana.lbl.gov/EisenSoftware.htm). Quantitative real-time PCR was performed on a PRISM 7900 sequenced detector (Applied Biosystems) using TaqMan probes (Applied Biosystems). Samples were normalized to the levels of 18S ribosomal RNA.

Chromatin Immunoprecipitaion (ChIP)

ChIP assays were performed as described previously. MCF-7 cell were treated with or without 3-deazaneplanocin (5 µM) for 48 hours. MCF-7 cell were seeded into 6-well plates at 30% confluence and treated with or without 3-deazaneplanocin (5 µM) for 48 hours. Cells were washed once in 1× phosphate-buffered saline (PBS) and then treated with 1% formaldehyde in PBS at 37° C. for 10 mM followed by the addition of glycine to a final concentration of 0.125 M for 5 mM. Cells were then scraped on ice and centrifuged at 1500 rpm for 5 mM at 4° C. After washing with PBS cell pellets were resuspended in 1 mL of cold lysis buffer (10 mM HEPES at pH 7.5, 1 mM EDTA at pH 8.0, 400 mM NaCl, 10% glycerol, 0.5% NP-40, 0.5 mM phenylmethylsulfonyl fluoride, and protease inhibitors [1 mM benzamidine, 3 mg/mL leupeptin, 0.1 mg/mL bacitracin, 1 mg/mL macroglobulin]) followed by centrifugation at 11,500 rpm in a microfuge for 5 min at 4° C. to remove protein not cross-linked to chromatin. The resulting pellets were then resuspended again in 1 mL of cold lysis buffer and sonicated with a Heat Systems-Ultrasonics, Inc. W-220 sonicator at 20% output for a total of 2 mM (pulsed: 30 sec on/30 sec off). The resulting solution was cleared by centrifugation at maximum speed in a microfuge for 10 mM at 4° C. At this point 5% of the solution was taken and stored at −20° C. for the input chromatin sample. The chromatin solution was precleared for 2-4 h with 80 µL of a 50% slurry of Protein A/G Sepharose beads (Pharmacia).

Pre-cleared chromatin from $2 \times 10^7$ MCF7 cells were immunoprecipitated with preblocked overnight at 4° C. with sheared salmon sperm DNA (0.3 mg/mL) and BSA (1 mg/mL) and then incubated with 5 µg anti-SUZ12 antibody (07-379, Upstate), 5 µg anti-RNA polymerase II (sc-899, Santa Cruz) and 5 µg of a non-specific IgG (sc-2027, Santa Cruz). Immunoprecipitations were performed overnight at 4° C. Immune complexes were eluted from the beads by adding 75 µL elution buffer (50 mM Tris at pH 8.0, 1% SDS, 10 mM EDTA at pH 8.0) and heating at 65° C. for 10 min. Elutions were performed twice and the eluates pooled. Cross-links were then reversed by placing the eluates at 65° C. overnight along with 5% of the cross-linked whole-cell extract sample diluted in the elution buffer (1:4) to generate the input chromatin samples. The DNA was then purified using the Qiagen QIAquick PCR, and PCR was performed using the Expand High Fidelity PCR system (Roche Biochemicals). Final primer concentration was 0.5 µM. Approximately 1% of the input chromatin sample and 10% of the ChIP sample were used as template in each reaction. Reaction mixtures were initially melted at 94° C. for 5 min followed by 27 cycles of 94° C./30 sec, 56° C./1 min, 72° C./1 min, and a final extension of 72° C. for 7 min. Amplicons are all in the 150-300-bp range. Samples were resolved on 3% agarose gels containing ethidium bromide. Primers used were of the following sequences:
TGFBI: forward 5'-ATGTCACTTGCCTCCACCCATC-3' (SEQ ID NO: 6) and reverse 5'-ACCTGCTCTGAGGCCTGAAAG-3' (SEQ ID NO: 7). IGFBP3: forward 5'-TTCACCCAAGGCTTCGTGCTG-3' (SEQ ID NO: 8) and reverse 5'-TCCGCGGGAGGAGACTTTCC-3' (SEQ ID NO: 9). KRT17: forward 5'-AACCCATTTCCCCACCAGACAGG-3' (SEQ ID NO: 10) and reverse 5'-AAATCCTCGTGCTGAGTGCCG-3' (SEQ ID NO: 11). FBXO32: forward 5'-GCAGGTGGGCATTGTGGAGC-3' (SEQ ID NO: 12) and reverse 5'-TGATGTACCCAGGGCCAATGC-3' (SEQ ID NO: 13). LAMB3: forward 5'-GCAGGTGGGCATTGTGGAGC-3' (SEQ ID NO: 14) and reverse 5'-TCCAGATCGCCTGAAAGCTCC-3' (SEQ ID NO: 15). ANXA8: forward 5'-GAATGATGAAAATGGGCTGGGTG-3' (SEQ ID NO: 16) and reverse 5'-GAAATTCTTAGCTCCAGCCTGCG-3' (SEQ ID NO: 17). TENS1: forward 5'-TGGCCTGGGAGCTTTCTTTACC-3' (SEQ ID NO: 18) and reverse 5'-TCTGGGCCAACGTTGCTTTG-3' (SEQ ID NO: 19). PLAU: forward 5'-GGAAGCACCAACAGTTTATGCCC-3' (SEQ ID NO: 20) and reverse 5'-ATCAGAGGGGGAAGGCAAGG-3' (SEQ ID NO: 22).

Depletion of PRC2 Proteins and the Inhibition of H3-K27 Methylation by 3-Deazaneplanocin A (DZNep)

Figure 1B:
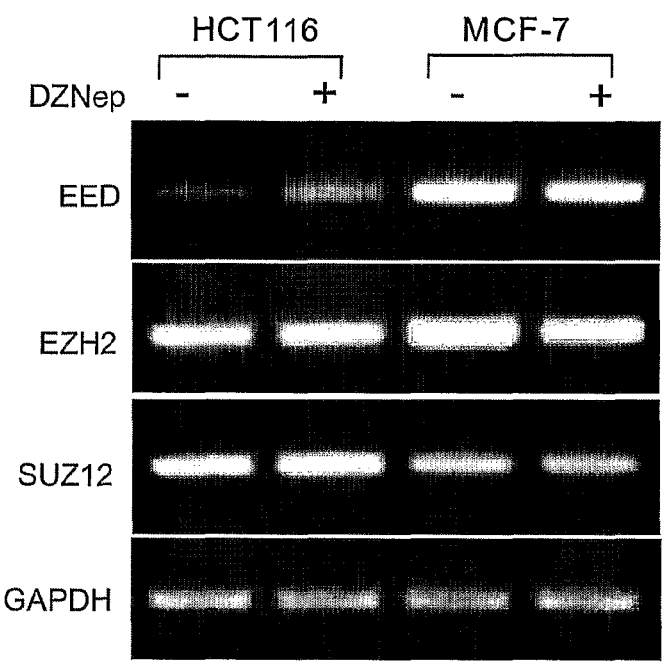
FIG. 1B depicts the analysis of the mRNA levels of the PRC2 proteins EZH2, SUZ12, and EED by reverse transcription (RT-PCR) before (−) and after (+)3-deazaneplanocin treatment. HCT116 cells were treated as in (a) and total RNA was isolated for RT-PCR analysis GAPDH served as a control.

As shown by Western blot analysis (FIG. 1A), treatment of HCT116 or MCF-7 cells with 5 µM 3-deazaneplanocin for 48 and 72 hours resulted in the dramatic decrease in protein levels of PRC2 components SUZ12, EZH2 and EED. Accordingly, trimethylation of histone 3 at lysine 27 (H3-K27) was strongly reduced by 3-deazaneplanocin. In contrast, histone H3 methylation at lysine 9 (H3-K9) was not affected by 3-deazaneplanocin treatment. This result is in agreement with the previous findings that H3-K27 is a specific substrate of PRC2 histone methyltransferase, whereas H3-K9 methylation is often mediated by Suv39h1 methyltransferase. Accordingly, it was found that Suv39h1 protein levels were not affected by 3-deazaneplanocin. In addition, 3-deazaneplanocin treatment did not affect histone acetylation and did not cause a change in DNMT1 or DNMT3B protein expression, which is known to be depleted by DNMT inhibitors such as 5-AzaC and Zebularine. The mRNA levels of each of the PRC2 proteins, as measured by polymerase chain reaction with reverse transcription (RT-PCR), however, remained unchanged after 3-deazaneplanocin treatment (FIG. 1B), suggesting that the decrease in PRC2 components occurs at the protein level and is not due to the inhibition of their transcription.

Figure 1C:
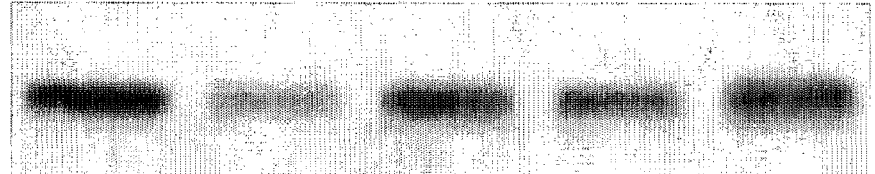
FIG. 1C depicts the effect of 3-deazaneplanocin in the presence of proteosome inhibitors on EZH2 and SUZ12 protein levels. MCF-7 cells were treated with 3-deazaneplanocin for 18 h, followed by the addition of proteosome inhibitor MG132 (5 µM), LLNL (50 µM), MG115 (20 µM) and (10 µM) for 8 h. Cells were harvested for Western blot analysis of EZH2 and SUZ12.
Figure 1C:
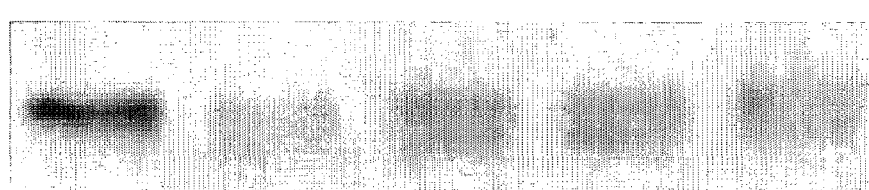
Figure 1C:
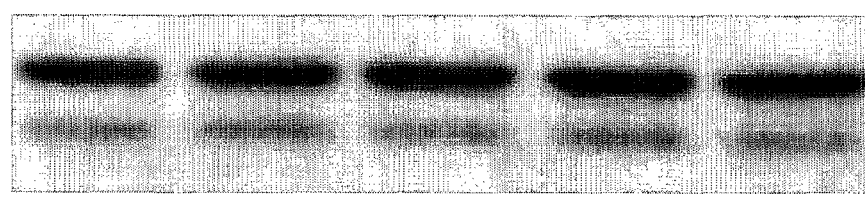

It has previously been reported that the stability of PRC2 proteins is regulated through proteosome-mediated mechanism. It was therefore tested whether the depletion of PRC2 proteins by 3-deazaneplanocin results from the protein degradation. MCF-7 cells were treated with 3-deazaneplanocin in the presence or absence of three individual proteosome inhibitors MG132, LLNL, and MG115 to test if these treatments would rescue 3-deazaneplanocin-induced PRC2 depletion. As shown in FIG. 1C, treatment with each proteosome inhibitor prevented the downregulation of EZH2 and SUZ12 protein levels in response to 3-deazaneplanocin. These results demonstrated that 3-deazaneplanocin depleted PRC2 proteins through increased protein degradation.

3-Deazaneplanocin Preferentially Induces Apoptosis in Cancer Cells

3-Deazaneplanocin was found to be able to induce cell death. It was observed that 3-deazaneplanocin at 5 µM could induce 25% cell death at 48 hours and 45% of cell death at 72 hours, as determined by propodium iodide (PI) staining and flow cytometry analysis (FIG. 3A). 3-Deazaneplanocin at 5 µM also induced obvious cell death in a variety of other cancer cell lines, including breast cancer MB-468 cells, colorectal cancer HCT116, RKO, and SW480 cells.

To elucidate the mechanisms by which 3-deazaneplanocin induces cell death, flow cytometry was used to analyse the loss of mitochondrial membrane potential ($\Delta\Psi m$) in MCF-7 and HCT116 cells after 3-deazaneplanocin treatment (FIGS. 3B & 3C). 3-deazaneplanocin induced a marked increase in the percentage of cells with lower $\Delta\Psi m$, indicating the mitochondrial damage in these cells after 3-deazaneplanocin treatment. Cleavage of caspase 9, and poly(ADP-ribose) polymerase (PARP) in 3-deazaneplanocin-treated cells was also easily detectable (FIG. 3D). These results show that 3-deazaneplanocin triggers an apoptotic cell death response involving mitochondria dysfunction and caspase activation.

To determine whether 3-deazaneplanocin preferentially induces apoptosis in cancer cells, the apoptosis induction between MCF-7 cells and the non-cancerous breast epithelial MCF10A cells was compared for various periods of time. While 3-deazaneplanocin treatment resulted in a progressive and marked apoptosis in MCF-7 cells, no obvious apoptosis was induced in MCF10A cells for up to 96 hours after 3-deazaneplanocin treatment (FIG. 3F). In addition, normal primary colon epithelial CC33D cells, like MCF10A cells, were also resistant to 3-deazaneplanocin treatment compared to colorectal cancer HCT116 cell, as evaluated by microscopy examination (FIGS. 3G & 3H). Therefore, 3-deazaneplanocin preferentially induced apoptosis in cancer cells.

To determine whether 3-deazaneplanocin induced-apoptosis is attributable to the depletion of PRC2 proteins, the PRC2 proteins (EZH2, EED, and SUZ12) were directly knocked down individually by treating MCF-7 cells with small interfering RNA (siRNA) oligonucleotides and examined their abilities to induce apoptosis. Western blot analysis of siRNA-treated MCF-7 cells confirmed the knockdown efficiency (FIG. 3I). Notably, knockdown of each of the PRC2 proteins resulted in the down regulation of the other two components, a result which is consistent with the previous finding that the protein levels of PRC2 components are dependent on the presence of the other members of the complex. As an expected result of PRC2 knockdown, histone H3-K27 trimethylation was markedly reduced, while the H3-K9 trimethylation remained the same. Induction of PARP cleavage was obvious under these conditions (FIG. 3I) and cells treated with each PRC2 siRNAs individually displayed substantial apoptosis (FIG. 3J). Thus, 3-deazaneplanocin-induced apoptosis is, at least in part, mediated through its ability to deplete the PRC2 complex and inhibit the associated histone H3-K27 methylation.

Identification of PRC2 Repressed Genes in Breast Cancer and Their Reactivation by 3-Deazaneplanocin PRC2 functions to suppress the expression of its target genes. Thus, the depletion of PRC2 by 3-deazaneplanocin is expected to result in their re-expression. Determining the 3-deazaneplanocin-activated PRC2 targets, required identifying the putative target genes suppressed by PRC2. The present example focuses on breast cancer cells, as PRC2 components EZH2 and SUZ12 have been reported to be overexpressed in breast tumours (Kirmizis et al., 2003, supra; Kirmizis et al., 2004, supra). siRNA was used to knock down the three core components of PRC2 (EZH2, SUZ12 and EED) individually in MCF-7 cells. The effects on gene expression were analysed using an Illumina Gene Expression BeadChip. Data analysis revealed that there were 708, 684 and 572 genes upregulated $\geq$2-fold after EZH2, EED or SUZ12 siRNA treatment, respectively. FIG. 4A shows an overlap of 450 genes upregulated in at least two siRNA conditions and 95 genes upregulated in all three of the siRNA experiments (p<0.0001 for both the two and three condition overlaps). In total, there were 1402 genes whose expression was increased upon depletion of at least one out of three PRC2 proteins. To be inclusive for the subsequent analysis, all 1402 genes were considered to be potential PRC2 target genes.

Furthermore array analysis was performed to identify the genes upregulated by 3-deazaneplanocin. Treatment of MCF-7 cells with by 3-deazaneplanocin for 72 h led to the upregulation of 750 genes $\geq$2-fold. To identify 3-deazaneplanocin-upregulated PRC2 target genes, the 750 genes inducible by 3-deazaneplanocin were compared with the 1402 candidate PRC2 target genes. An overlap of 140 genes (p<0.0001, FIG. 4B) was identified. These overlap genes are candidate PRC2 target genes whose expression can be activated by 3-deazaneplanocin.

Figure 4D:
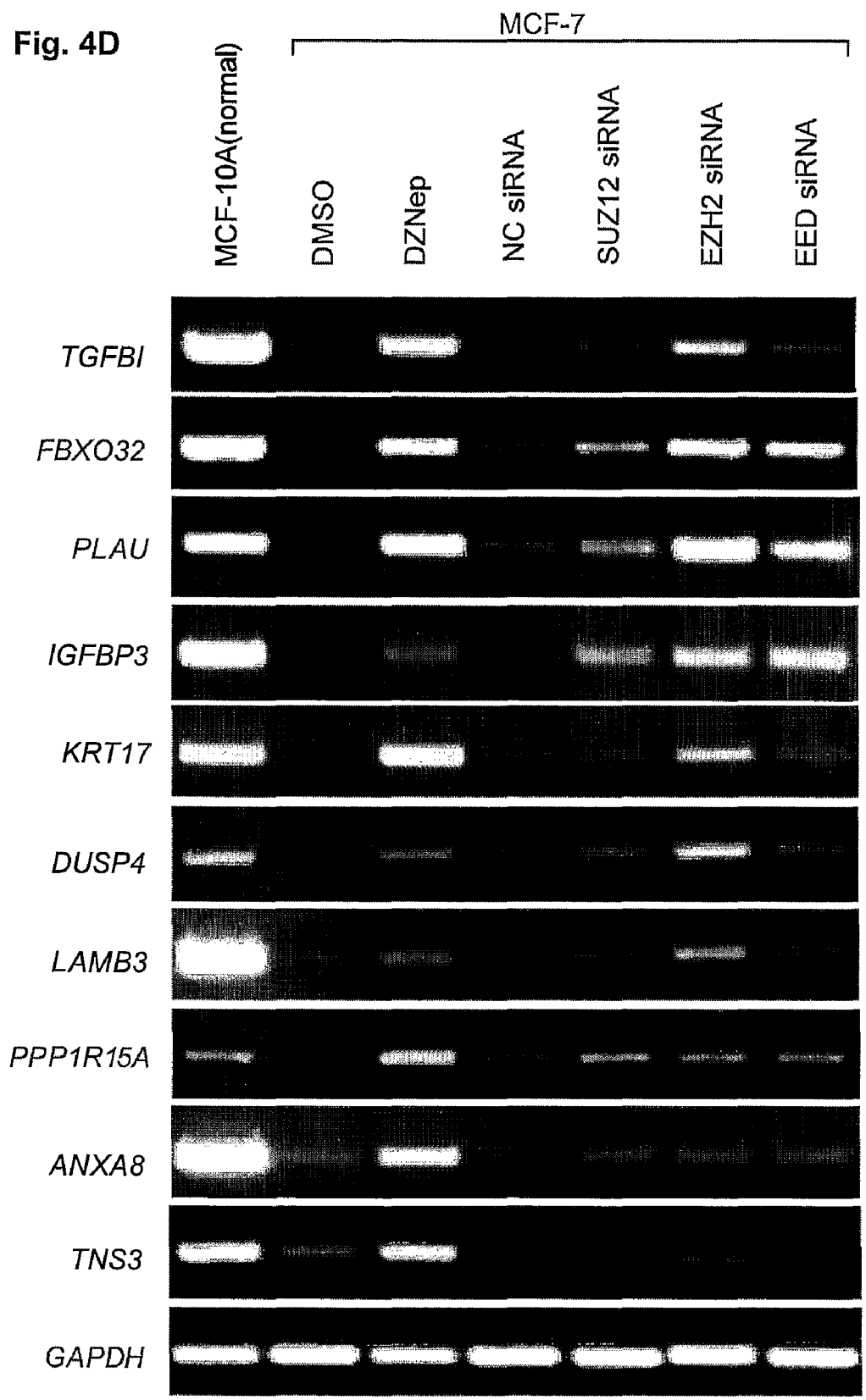

Because 3-deazaneplanocin preferentially induced apoptosis in MCF-7 compared to non-cancerous MCF10A cells, PRC2 target genes might be differentially expressed between cancerous and non-cancerous cells. To identify the PRC2 targets specifically repressed in breast cancer cells, the expression profiles of the 140 putative PRC2 target genes in MCF-7 cells and MCF10A cells were compared by gene clustering analysis (FIG. 4C). This analysis led to the identification of a set of 47 out of 140 genes that were expressed at least two fold lower in MCF-7 cells relative to the MCF10A cells, whereas the rest of the putative PRC2 target genes either were expressed in similar levels between the two cell types or even expressed in higher levels in MCF-7 cells (FIG. 4C, left panel). 3-deazaneplanocin treatment or siRNA knockdown of PRC2 proteins resulted in their re-expression in MCF-7 cells (FIG. 4C, right panel). To verify the reliability of the gene array data semi-quantitative RT-PCR of 10 random selected genes from the 47-gene set was performed (FIG. 4D). In each case, the candidate gene was highly expressed in MCF10A cells but had low or undetectable expression in MCF-7 cells. 3-deazaneplanocin treatment or siRNA depletion of the PRC2 proteins resulted in their re-expression in MCF-7 cells.

Figure 4F:
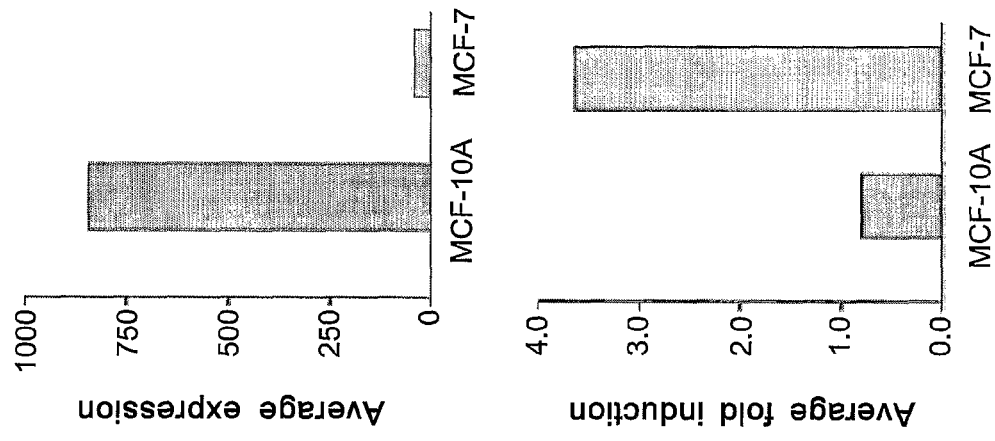
Figure 4E:
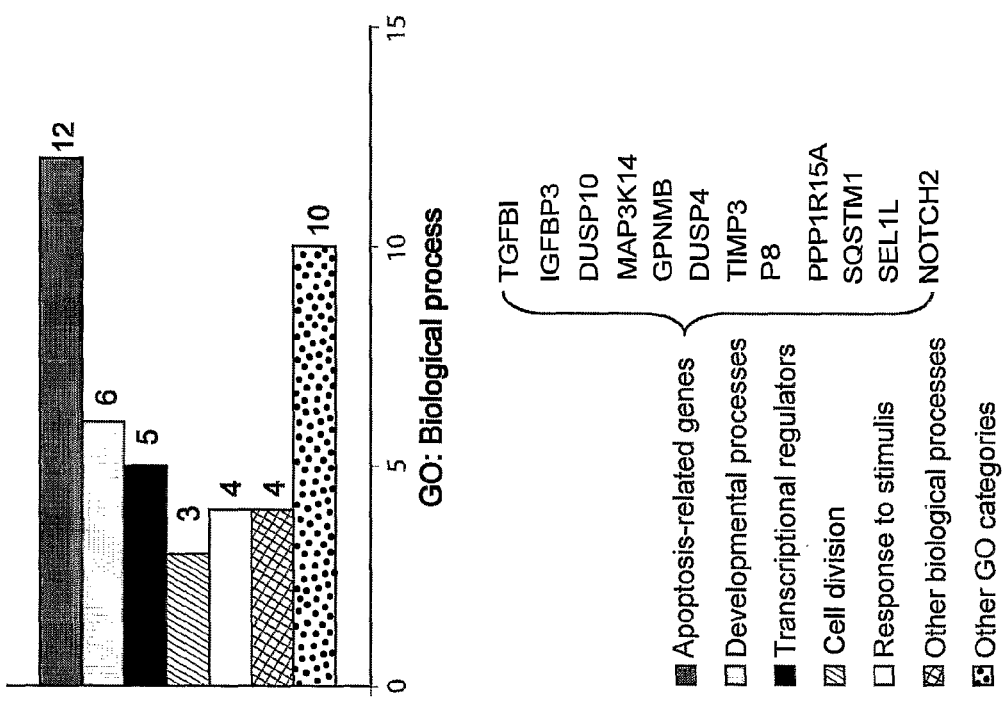

By using such stringent criteria, a cohort of PRC2 target genes was uncovered that are specifically repressed in breast cancer cells. Gene ontology (GO) analysis has revealed that these genes were remarkably enriched for their roles in growth inhibition or apoptosis, as seen in TGFBI and IGFBP3 (FIG. 4E). Thus, these genes are likely to be putative tumour suppressors of the malignant phenotype epigenetically silenced or repressed by PRC2 in breast cancers. In addition, genes that were highly suppressed by PRC2 in MCF-7 cells were preferentially reactivated by 3-deazaneplanocin. This is in striking contrast to MCF10A cells where these genes were already expressed at high levels and did not undergo further induction (FIG. 4F). This might explain the lack of sensitivity of MCF10A cells in response to 3-deazaneplanocin treatment, and implies that cancer selectivity of 3-deazaneplanocin might lie in the preferential reactivation of PRC2-repressed genes in cancer cells.

Figure 4G:
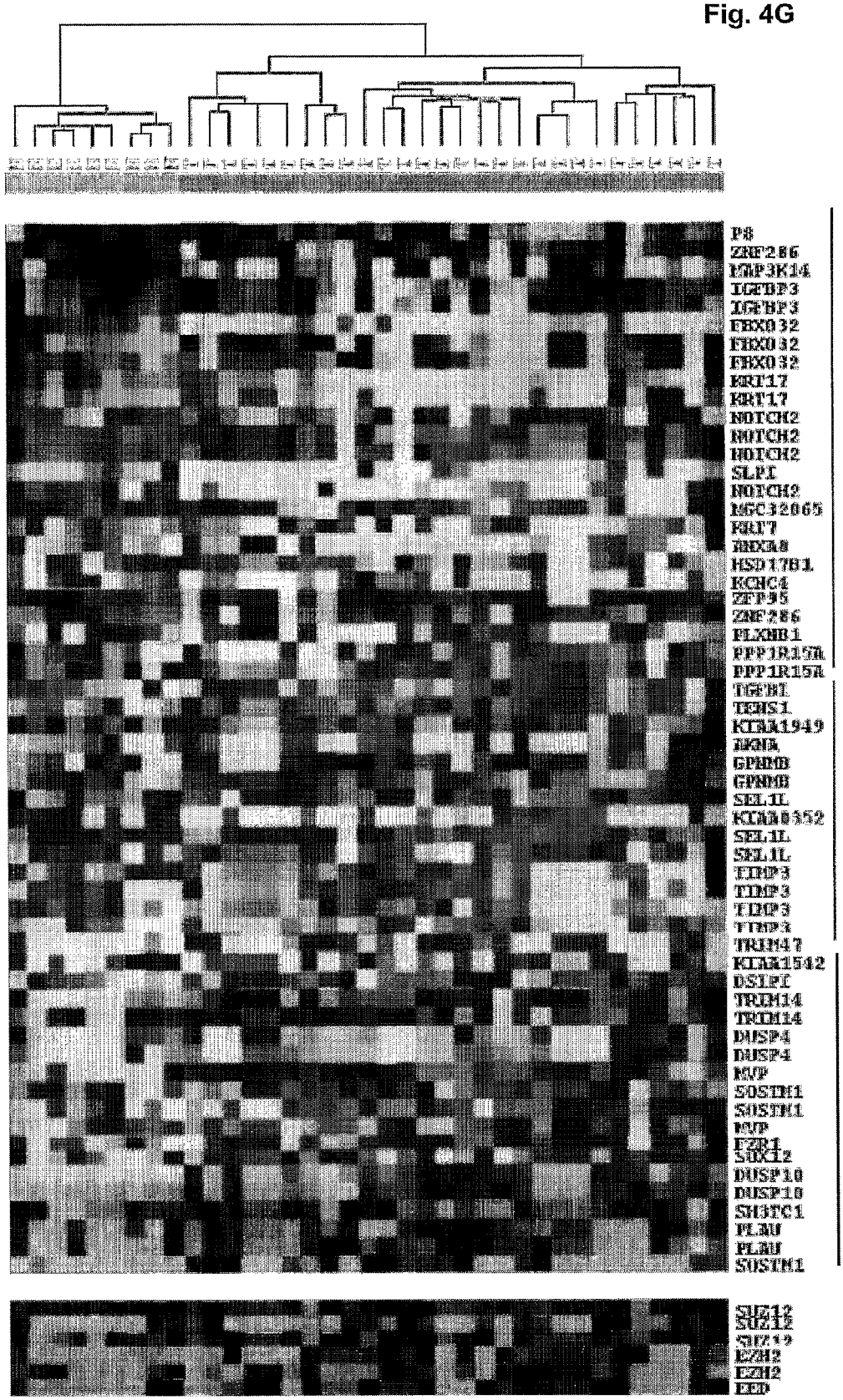

Furthermore the gene expression analysis was conducted on a data set consisting of a collection of 28 primary breast tumour samples and 9 normal breast tissues. The 47 cancer-specific PRC2-repressed genes, together with EZH2, SUZ12 and EED, were included for the analysis. Unsupervised cluster analysis indicated that 34 unique probes present in this Affymetrix array data set clearly separated the tumour and normal samples (FIG. 4G). A subset of 17 genes (Cluster I) showed lower expression in breast tumours relative to the normal breast tissues, which, as expected, was correlated with the higher EZH2 and SUZ12 expression. This data shows that this subset of PRC2 targets are the clinically relevant ones repressed in primary human breast cancers. The rest of the genes were either less distinguishable between tumour or normal tissues (cluster II) or even expressed in higher levels in tumours (cluster III). Thus, these genes might not reflect the PRC2-mediated epigenetic changes in primary tumours.

Guided by pharmacological, genomic, and functional analysis, group of putative clinically relevant PRC2 targets was thus identified. Integration of in vitro and in vivo studies enabled a significant pairing of the PRC2 target list to genes pertinent in primary breast tumours. For instance, PLAU and DUSP4 & 10 were silenced in MCF-7 cells but were actually found to be expressed at higher levels in primary tumour samples compared to the normal tissues. Though this may reflect fundamental differences between cancer cells lines and primary breast cancer cells, it is equally likely that expression of these "discordant" genes (e.g. PLAU and DUSP4 & 10) is due to the non-cancerous components of primary tumours such as macrophages, vascular cellular components, and stromal cells. Nevertheless, through this selection, we identified a group of clinically relevant PRC2 targets whose expression was consistently down-regulated in primary breast tumours relative to the normal breast tissues. Many PRC2-repressed target genes, such as TGFBI, IGFBP3, and PPPIR15A are known to have functions in growth inhibition or apoptosis, suggesting their potential roles as putative tumour suppressors. Re-expression of these genes might collectively contribute to 3-deazaneplanocin-induced apoptosis.

Effects of 3-Deazaneplanocin on PRC2 Targets Promoter Occupancy by PRC2 and RNA Polymerase II Chromatin immunoprecipitation (ChIP) was used to determine whether PRC2 binds to its putative target gene promoters, and whether or not this binding can be affected by 3-deazaneplanocin treatment. Furthermore the binding of RNA polymerase II (RNA Pol II) was analysed, as RNA Pol II and PRC2 bind to gene promoters in a mutually exclusive manner (Vire et al., 2006, supra). It was reasoned that the depletion of PRC2 by 3-deazaneplanocin would lead to increased RNA Pol II recruitment to the PRC2 target gene promoters. The ChIP PCR primers within the 8 candidate PRC2 target gene core promoter regions were designed, since 95% of the PRC2 binding sites were previously found within 1 kb of transcription start sites with or without a CpG island (Lee et al., 2006, supra) (FIG. 5A). As evidenced by ChIP analysis performed using SUZ12 and RNA Pol II antibodies, untreated MCF-7 cells displayed strong binding of SUZ12 to the examined PRC2 target gene promoters, whereas only background or minimal binding was detected in non-specific IgG or RNA Pol II pull-down samples (FIG. 5B). Following treatment with 3-deazaneplanocin, SUZ12 binding to these promoters was markedly reduced, whereas the binding of RNA Pol II was increased. Taken together with the re-expression of these genes after depletion of PRC2 by 3-deazaneplanocin, these findings confirmed that PRC2 binding to these gene promoters is required for their transcriptional repression. Disruption of PRC2 proteins by 3-deazaneplanocin reduced this binding, resulting in the increased recruitment of RNA Pol II and activation of PRC2 target gene promoters.

Reactivation of PRC2-Repressed Targets by 3-Deazaneplanocin is not the Result of Inhibition of DNA Methylation Since 3-deazaneplanocin inhibits AdoHyc hydrolase activity and indirectly causes inhibition of general methylation reaction, there is the possibility that 3-deazaneplanocin-mediated reactivation of PRC2 target genes might be the result of DNA hypomethylation. It was therefore tested whether treatment of MCF-7 cells with DNA demethylating agent 5-aza-2'deoxy-cytidine (5-AzaC) or in combination with histone deacetylase inhibitor trichostatin A (TSA) was be able to activate these genes. Array analysis was performed in MCF-7 cells treated with either 5-AzaC alone or in combination with TSA. The expression profiles of 140 previously identified PRC2 targets were compared with MCF-7 cells treated with 3-deazaneplanocin. FIG. 5C (I) shows that the above treatments did not result in the significant reactivation of the PRC2 targets in general in comparison with the 3-deazaneplanocin treatment. Among 140 PRC2 target genes, only 13 genes (~10%) showed an induction of $\geqq$3-fold after combined treatment of 5-AzaC and TSA (such as ANAX8 and DLX2), suggesting that it is possible that for some of the PRC2 targets 3-deazaneplanocin might increase their expression as a result of DNA demethylation. The array results were further confirmed by real-time RT-PCR for representative PRC2 targets. Genes such as TGFBI, KRT17 and FBX032 were only induced by 3-deazaneplanocin, but not by 5-AzaC with or without TSA (FIG. 5C, II). Expressions of ANXA8 and DLX2, however, were activated by both 3-deazaneplanocin and co-treatment of 5-AzaC and TSA (FIG. 5C, III). These data showed that the reactivation of PRC2 target genes by 3-deazaneplanocin was not the result of DNA hypomethylation in general, though there might be exceptions for certain PRC2 target genes such as ANXA8 and DLX2. For these genes, PRC2 might recruit DNMT to their promoters and coordinately suppress their expression, as suggested by a recent study (Vire et al., 2006, supra).

Identification of the PRC2 Target Genes Associated with Cellular Sensitivity to 3-Deazaneplanocin To extend the observation seen in MCF-7 cells, additional breast cancer cell lines were screened, including MB-468, SK-BR-3, MB-231, T47D and BT549. The apoptotic response in a time course analysis revealed that the collected breast cancer cell lines exhibited varied sensitivity to 3-deazaneplanocin. Similar to MCF-7 cells, MB-468, SK-BR-3, and T47D cells were highly susceptible to 3-deazaneplanocin-induced cell death. In contrast, MB-231 and BT-549 cells, together with MCF10A, were highly resistant to the 3-deazaneplanocin treatment (FIG. 6A). To identify the PRC2 target genes associated with the cellular sensitivity to 3-deazaneplanocin, the array analysis was performed in these breast cancer cell lines before and after 3-deazaneplanocin treatment and the expression of the 47 identified PRC2 targets profiled. It was reasoned that some the PRC2 target genes might be differentially expressed between the sensitive and resistant cell lines, which might confer the distinct sensitivity to 3-deazaneplanocin. Gene clustering analysis revealed that a subset of PRC2 targets (22 genes) were expressed in consistent high levels in resistant cell lines (MCF10A, MB-231, and BT549), but were expressed in lower levels in sensitive cell lines (MCF-7, MB-468, SK-BR-3 and T47D) (FIG. 6B). Among this set of genes, four genes: FBXO32, LAMB3, PLAU, and PPP1R15A were found to be commonly induced by 3-deazaneplanocin in all the four sensitive cell lines and four additional genes (TGFBI, IGFBP3, TNS3 and KRT17) were induced in 3 out 4 sensitive cell lines. In resistant cell lines (MCF10A, MB-231, and BT549), however, these genes were already highly expressed (except LAMB3 in BT549) and did not undergo marked further induction after 3-deazaneplanocin treatment. Both the real time and conventional RT-PCR analysis of the 4 gene set confirmed the array data (FIGS. 6D & 6E). Therefore, the suppressed expression of these genes and the extent of their induction by 3-deazaneplanocin appeared to be associated with the cellular sensitivity to 3-deazaneplanocin. Notably, however, the expression levels of the PRC2 targets were not always associated with the levels of PRC2 proteins. For instance, in MB-231 cells that seemed to express a higher level of EZH2 protein, many PRC2 targets were not necessarily suppressed (FIG. 6E, lower panel). This indicates that in these cells EZH2 might not be functional or require additional factors such as DNMT and HDAC to help establish and maintain the epigenetic control of these genes.

To determine the functional roles of the above PRC2 target genes in 3-deazaneplanocin-induced apoptosis, siRNAs were used to prevent the induction of the 7 PRC2 targets associated with the 3-deazaneplanocin response, and their effects on apoptosis induction by 3-deazaneplanocin evaluated. Only FBXO32 siRNA treatment decreased the apoptotic response to 3-deazaneplanocin. The rest of the siRNA oligonucleotides targeting other 6 PRC2 targets did not appear to inhibit 3-deazaneplanocin-induced apoptosis (FIG. 6F). To eliminate the off-target effect of siRNA, a different FBXO32 siRNA was additionally used. It was confirmed that inhibition of FBXO32 induction resulted in significant attenuation of apoptosis induction by 3-deazaneplanocin (FIG. 6G). Similar results were also observed in MB-468 and T47D cells (data not shown). These experiments identify FBXO32, among the identified PRC2 targets, as the key effector mediating the 3-deazaneplanocin-induced apoptosis in breast cancer cells. Therefore, the silence status of FBXO32 in breast cancer cells and its reactivation by 3-deazaneplanocin appears to be an important determinant of 3-deazaneplanocin response. Moreover, the functional role of FBXO32 as a potential tumour suppressor was further supported by its ability to affect colony formation. FIG. 6H shows that transfection of FBXO32 in MCF-7 cells caused a substantial reduction in the number of colonies formed compared to cells transfected with a control vector.

Without the intent of being bound by theory or to the above examples, it is noted that 3-deazaneplanocin, as an AdoHcy hydrolase inhibitor, interferes with the AdoMet-AdoHcy metabolism and can cause reduced methylation reaction (Glazer, R I, et al., Biochem Biophys. Res. Commun. (1986), 135, 2, 688-694). Unlike a DNA hypomethylating agent, such as 5-aza-2'deoxy-cytidine or zebularine that deplete DNMTs, this compound appeared to have no effect on DNMTs but induced efficient depletion of the PRC2 proteins and the associated histone-H3K27 methylation. The effect of 3-deazaneplanocin on PRC2 appeared to be selective, since it had no effect on Suv39h1 or on the associated H3-K9 methylation. The depletion of PRC2 proteins after 3-deazaneplanocin treatment is not achieved through transcriptional inhibition since 3-deazaneplanocin treatment did not affect their mRNA levels. Instead, it proceeds through the proteosomal degradation since proteosome inhibitors can restore the protein expression. Unlike 5-AzaC and Zebularine that depletes DNMTs through their incorporating into DNA and thus trapping of the enzymes to the substituted DNA (Cheng et al., 2004, supra), 3-deazaneplanocin is not phosphorylated and does not get incorporated into DNA (Glazer et al., 1986; Tseng et al., 1989). Thus it seems highly unlikely that 3-deazaneplanocin depletes PRC2 proteins through the similar mechanism. It has been reported that the integrity of this complex depends on the existence of each component and that the knockdown of one component will lead to the protein downregulation of the others (Pasini, D., et al., EMBO Journal (2004) 23, 4061-4071). Given the efficient depletion of all three of the PRC2 proteins by 3-deazaneplanocin, it is possible that 3-deazaneplanocin might primarily affect one component, which would subsequently result in the downregulation of others. Alternatively, it is possible that the inhibition of S-adenosyl-methionine incorporation to histone H3-K27 might reduce the binding of PRC2 proteins to chromatin and thus affects its stability.

Through gene expression analysis of a collection of breast cancer cell lines that are sensitive or resistant to 3-deazaneplanocin, the inventors have been able to define the PRC2 targets that are most likely associated with the cellular response to 3-deazaneplanocin. This small set of genes might serve as a surrogate marker to predict the response of 3-deazaneplanocin in breast cancer cells and guide the selection of the subset of breast cancer patients for the PRC2-targeted therapy in the future. Moreover, further functional analysis using RNA interference identifies that the re-expression of FBXO32, which encodes the F-box protein 32, contributes at least in part to the apoptotic response of 3-deazaneplanocin. Its potential function as a tumour suppressor was further supported by its ability to suppress the cell growth and colony formation. Importantly, FBXO32 is confirmed to be strongly repressed in primary breast tumours relative to the normal tissues. Therefore, the selective repression of some of the potential tumour suppressors by PRC2 in human breast cancers but not in normal tissue, and its effective reversal by PRC2 targeting agents, points to a novel therapeutic approach leading to the preferential killing of tumour versus non-tumour cells.

It has been recently reported that PRC2 directly controls DNA methylation through interacting with DNMT (Vire et al., 2006, supra). Although 3-deazaneplanocin might inhibit all the methylation reaction, we found that its ability to activate the PRC2-repressed genes is not associated with possible inhibition of DNA methylation in general. However, we did find that a small portion of the PRC2 target genes (~10%) whose expression can be enhanced by treatment with 5'-AzaC and TSA, suggesting that for these genes PRC2 might require DNMT to control their expression. Therefore, 3-deazaneplanocin distinguishes from other chromatin remodelling agents such as DNMT and HDAC inhibitors and appeared to be the first compound thus far that can reactivate gene expressing by modulating PRC2 and associated histone methylation. Up until now, 3-deazaneplanocin has been explored for antiviral treatment (De Clercq, E. D., et al., Antimicrobial Agents & Chemotherapy (1989) 33, 8, 1291-1297) and was shown to have minimal toxicity in vivo. Regardless of the exact mechanism, its intriguing apoptotic activity in cancer cells, as first described in this study, together with the important cancer pathway it affects, makes it a promising drug candidate for anti-cancer treatment.

Moreover, in addition to its potential use as a novel anticancer compound, 3-deazaneplanocin can also serve as a useful tool for epigenetic study.

The listing or discussion of a previously published document in this specification should not necessarily be taken as an acknowledgement that the document is part of the state of the art or is common general knowledge.

The inventions illustratively described herein may suitably be practiced in the absence of any element or elements, limitation or limitations, not specifically disclosed herein. Thus, for example, the terms "comprising", "including," "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by exemplary embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims. In addition, where features or aspects of the invention are described in terms of Markush groups, those skilled in the art will recognize that the invention is also thereby described in terms of any individual member or subgroup of members of the Markush group.

What is claimed is:

1. An epigenetic method of inducing apoptosis in a tumour cell by inhibition of histone methylation, said method comprising administering to said tumour cell a compound of the general formula (I)

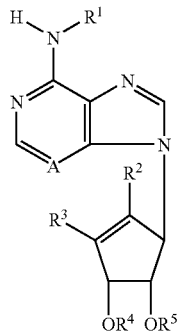

wherein in formula (I)
A is C or N,
$R^1$, $R^4$ and $R^5$ are independently selected from the group consisting of H and aliphatic, cycloaliphatic, aromatic, arylaliphatic, and arylcycloaliphatic hydrocarbyl groups, comprising 0-3 heteroatoms selected from the group N, O, S, and Si, wherein $R^4$ and $R^5$ may optionally be linked so as to define an aliphatic hydrocarbyl bridge,
$R^2$ is selected from the group consisting of H and halogen, and
$R^3$ is H, or an aliphatic or arylaliphatic hydrocarbyl group comprising 1-8 main chain carbon atoms and 0-3 heteroatoms selected from the group N, O, S, Si, and halogen.

2. The method of claim 1, wherein said tumour cell is cultured.

3. The method of claim 1, wherein said tumour cell is a breast cancer cell.

4. The method of claim 3, wherein said cell is a cell selected from the group of cell lines consisting of MCF-7, MB-468, SK-BR-3, and T47D.

5. The method of claim 1, further comprising determining apoptosis in said tumour cell.

6. The method of claim 1, wherein said tumour cell is obtained from a mammal.

7. The method of claim 1, wherein said tumour cell is comprised in a mammal.

8. The method of claim 6, wherein the mammal is selected from the group consisting of a rat, a mouse, a cow, a pig and a human.

9. The method of claim 1, comprising contacting said tumour cell with a predetermined quantity of a compound of the general formula (I).

10. The method of claim 1, comprising the use of at least two different predetermined quantities of a compound of the general formula (I) and at least a first and a second tumour cell, wherein the first tumour cell is contacted with the lower of the two predetermined quantities and the second tumour cell is contacted with the higher of the two predetermined quantities.

11. The method of claim 10, wherein the first tumour cell and the second tumour cell are obtained from the same patient.

12. The method of claim 11, wherein said method is a method for predicting a patient's individual response to a compound of the general formula (I).

13. The method of claim 1, wherein said inhibition of histone methylation comprises an inhibition of methylation of lysine 27 on histone 3.

14. The method of claim 1, wherein said inhibition of histone methylation comprises depleting in the respective cell a polycomb repressive complex.

15. The method of claim 14, further comprising measuring the levels of at least one component of at least one polycomb repressive complex.

16. The method of claim 15, further comprising comparing the result of the measurement of levels of said at least one component of at least one polycomb repressive complex with that of a control measurement.

17. The method of claim 14, wherein depleting said polycomb repressive complex releases a complex between said polycomb repressive complex and a tumour suppressor gene.

18. The method of claim 17, wherein apoptosis is achieved by means of reactivating a tumour suppressor gene.

19. The method of claim 18, wherein said tumour suppressor gene is FBX032.

20. The method of claim 19, further comprising measuring the expression of FBX032 in the respective cell.

21. The method of claim 20, further comprising comparing the result of the measurement of FBX032 expression with that of a control measurement.

22. The method of claim 1, wherein said inhibition of histone methylation comprises modulating gene expression in a cell that expresses the components of a polycomb repressive complex.

23. The method of claim 22, wherein said polycomb repressive complex is at least one of polycomb repressive complex 2, polycomb repressive complex 3, and polycomb repressive complex 4.

24. The method of claim 22, wherein the cell is a recombinant cell comprising a target gene under the control of the promoter of the FBX032 gene.

25. The method of claim 22, wherein the target gene, the expression of which is modulated, is any one of a reporter gene, a drug resistance gene, an apoptosis gene (so-called 'death' gene), or any other gene with desirable expression in a respective cell.

26. The method of claim 1 wherein the step of administering comprises administering the compound of general formula (I) to a patient comprising said tumour cell.

* * * * *